United States Patent
Kennedy et al.

(10) Patent No.: US 8,702,810 B2
(45) Date of Patent: Apr. 22, 2014

(54) BIO-ARTIFICIAL PANCREAS AND A PROCEDURE FOR PREPARATION OF SAME

(75) Inventors: Joseph P. Kennedy, Akron, OH (US); Gabor Erdodi, Stow, OH (US); Mukerrem Cakmak, Monroe Falls, OH (US); Baris Yalcin, Akron, OH (US); Jungmee Kang, Stow, OH (US)

(73) Assignee: The University of Akron, Akron, OH (US)

( * ) Notice: Subject to any disclaimer, the term of this patent is extended or adjusted under 35 U.S.C. 154(b) by 972 days.

(21) Appl. No.: 12/529,732

(22) PCT Filed: Mar. 10, 2008

(86) PCT No.: PCT/US2008/003146
§ 371 (c)(1),
(2), (4) Date: Dec. 23, 2009

(87) PCT Pub. No.: WO2008/112190
PCT Pub. Date: Sep. 18, 2008

(65) Prior Publication Data
US 2010/0150984 A1    Jun. 17, 2010

Related U.S. Application Data

(60) Provisional application No. 60/906,142, filed on Mar. 9, 2007, provisional application No. 60/966,843, filed on Aug. 29, 2007.

(51) Int. Cl.
*A61F 2/02* (2006.01)
*A61K 9/24* (2006.01)

(52) U.S. Cl.
USPC ........ 623/23.64; 424/93.7; 424/424; 977/904

(58) Field of Classification Search
None
See application file for complete search history.

(56) References Cited

U.S. PATENT DOCUMENTS

| | | | |
|---|---|---|---|
| 4,378,016 A | 3/1983 | Loeb | |
| 4,588,461 A | 5/1986 | Braun | |
| 4,904,421 A | 2/1990 | Ando | |
| 5,262,055 A | 11/1993 | Bae | |
| 6,060,640 A * | 5/2000 | Pauley et al. | 623/23.72 |
| 2004/0037813 A1 * | 2/2004 | Simpson et al. | 424/93.7 |
| 2004/0148015 A1 * | 7/2004 | Lye et al. | 623/1.15 |
| 2004/0241436 A1 | 12/2004 | Hsieh | |
| 2009/0196901 A1 * | 8/2009 | Guilak et al. | 424/423 |

FOREIGN PATENT DOCUMENTS

| | | |
|---|---|---|
| WO | 2006073499 | 7/2006 |
| WO | 2008019044 | 11/2009 |

OTHER PUBLICATIONS

Huang et al., "A review on polymer nanofibers by electrospinning and their applications in nanocomposites", Composites Science and Technology, 2003, vol. 63, pp. 2223-2253.*
Thefreedictionary, http:// medical-dictionary.thefreedictionary.com/ p/perforated , 2013, Dictionary definition of Perforated, p. 1.*

* cited by examiner

*Primary Examiner* — Laura Schuberg
(74) *Attorney, Agent, or Firm* — Renner Kenner Greive Bobak Taylor & Weber

(57) ABSTRACT

The present invention generally relates to implantable devices for producing insulin in diabetic animals and to methods of making same. Some embodiments include amphiphilic biomembranes for use in biological applications (e.g., as an alternative and/or supplemental insulin source). Some embodiments also include live insulin-producing cells contained within one or more amphiphilic membranes so as to prevent or diminish an immuno-response and/or rejection by the host.

30 Claims, 17 Drawing Sheets

D₅H    PMHS    crosslinking site

BIO-ARTIFICIAL PANCREAS AND A PROCEDURE FOR PREPARATION OF SAME

The present invention was made in the course of research that was supported by National Science Foundation (NSF) Grant DMR 02-43314. The United States government may have certain rights to the invention or inventions herein.

RELATED APPLICATION DATA

This patent application is related to U.S. Provisional Patent Application No. 60/840,828, filed Aug. 29, 2006 and entitled "Implantable Devices for Producing Insulin;" and its PCT counterpart PCT Patent Application No. PCT/US07/018,975, filed Aug. 29, 2007 entitled "Implantable Devices for Producing Insulin;" and to PCT Publication No. WO 2008/019044, filed Aug. 3, 2007 and entitled "Amphiphilic Grafts and Co-Networks and Process for Making Same." All of the above identified patent applications are hereby incorporated by reference herein in their entireties.

FIELD OF THE INVENTION

The present invention generally relates to implantable devices for producing insulin in diabetic animals and to methods of making same. Some embodiments include amphiphilic biomembranes for use in biological applications (e.g., as an alternative and/or supplemental insulin source). Some embodiments also include live insulin-producing cells contained within one or more amphiphilic membranes so as to prevent or diminish an immuno-response and/or rejection by the host.

BACKGROUND OF THE INVENTION

Many medical deficiencies and diseases result from the inability of cells to produce normal biologically active compounds. Many of these deficiencies can be remedied by implanting a source of the needed biologically active compounds and/or pharmaceutical agents into the individual having the deficiency. A well known disease that can be remedied by implanting biological material and/or a pharmacological agent is Type I diabetes mellitus, wherein the production of insulin by pancreatic Langerhans islet cells is substantially deficient, impaired, or nonexistent.

Type I or insulin dependent diabetes mellitus (IDDM) is a major, expensive public health problem causing renal and vascular disease, heart disease, blindness, nerve damage, major disability, and premature death. One treatment approach is the transplantation of insulin producing pancreatic islet cells (9,000 to 12,000 islets/kg), which can return blood sugar levels to normal and free patients from the need to take exogenous insulin. If blood sugars, insulin, and C-peptide levels can be normalized at an early stage of the disease, the complications of diabetes can be avoided. Major barriers to the clinical application of islet cell transplantation have been the problems of graft rejection, the scarcity of human organs, and the expense of their procurement. The medications used to prevent rejection are costly, increase the risk of infection, and can, themselves, induce hyperglycemia, hyperlipidemia, hypertension, and renal dysfunction, although progress is being made towards less toxic drug regimens.

Injection of islet cells is appealing because it is less invasive than whole organ pancreatic grafts and entails a lower morbidity rate. Transplanted human islets (allografts) have been shown to survive in the liver after administration of immunosuppressive drugs, but reliable long term function has been difficult to achieve. Injection into the liver is usually accompanied by heparinization to avoid thrombosis, which can increase the risk of ocular complications. Furthermore, human islets are a scarce and expensive cell type. Therefore, many researchers have suggested using animal cells (xenografts), particularly porcine islets. Pigs are plentiful, although porcine islets are relatively difficult to isolate and are fragile.

Unfortunately, the immunologic barriers to the successful transplantation of xenografts are even more difficult to surmount than those for the transplantation of allografts. Humans have natural pre-formed antibodies that can react with a saccharide, Gal alpha 1,3Gal(Gal), expressed on the cells of lower mammals to trigger hyperacute rejection. In addition, the complement regulatory proteins (decay accelerating factor, membrane cofactor protein, CD59) that normally help to control damage induced by complement activation cannot function because they are species specific.

In light of the above hypothesis the immunoisolation of living allogeneic or xenogeneic insulin-producing islet cells by semi-permeable membranes may provide a means for correcting diabetes mellitus. In order to avoid hyperacute rejection, the recipient's antibodies should be prevented from "seeing" the foreign proteins and activating complement. The encapsulating material should also reliably safeguard the patient from infectious processes (e.g., bacteria) unwittingly transferred with the animal cells. Materials used for immunoisolation should allow insulin, glucose, oxygen, and carbon dioxide to pass freely. These molecules have diameters less than 35 Angstroms (3.5 nm). Studies suggest that pore diameters of 30 nm can exclude the immigration of immunoglobulins, complement, and cytokines (e.g., tumor necrosis factor) providing immunoisolation. Unless immune tolerance can be established, such membranes should also prevent the out-migration of xeno-antigens into the host where they can activate the indirect pathway resulting in T helper cell activation. Immune graft rejection by direct cytotoxicity appears to be a major cause for loss of transplanted cells since donor cell viability is better in immune-compromised ($CD4^+$ T cell depleted) mice. In addition, $CD4^+$ cells secrete interferon-[gamma] that attracts and activates macrophages and NK cells. Macrophages, in turn, recruit T-cell help and initiate rejection. B-cell humeral mediated immunity also plays a role in xenograft rejection. There is, however, ample evidence that the immune response is not the sole source of xenograft failure.

Researchers, working with ovarian cell xenografts microencapsulated in HEMA (hydroxyethyl methacrylate-methyl methacrylate), found that cells began to lose function before the antibody response occurred. Other causes of graft failure include an inflammatory response to the chemistry of the encapsulating material, nutrient deficiency, accumulation of waste products and free radicals within the encapsulating material, and inadequate oxygen delivery.

In view of the foregoing, there is a need in the art for improved methods and/or implantable devices for providing insulin to treat and/or cure diabetes.

SUMMARY OF THE INVENTION

The present invention generally relates to implantable devices for producing insulin in diabetic animals and to methods of making same. Some embodiments include amphiphilic biomembranes for use in biological applications (e.g., as an alternative and/or supplemental insulin source). Some embodiments also include live insulin-producing cells contained within one or more amphiphilic membranes so as to prevent or diminish an immuno-response and/or rejection by the host.

In one embodiment, the present invention relates to a method for producing an implantable device for providing insulin comprising: (A) providing at least one implantable device for producing insulin, the device comprising: a perforated mid-section bound at the edges thereof by a seal; and at least one filling port designed to permit the perforated mid-section to be filled with insulin producing cells; (B) depositing on the perforated mid-section a biologically compatible polymer network; and (C) forming at least one immunoisolatory membrane on the perforated mid-section.

In another embodiment, the present invention relates to a method for producing an implantable device for providing insulin comprising: (a) providing at least one implantable device for producing insulin, the device comprising: a perforated mid-section bound at the edges thereof by a seal; and at least one filling port designed to permit the perforated mid-section to be filled with insulin producing cells; (b) depositing on the perforated mid-section a biologically compatible polymer network; (c) forming at least one immunoisolatory membrane on the perforated mid-section (d) implanting the device into a diabetic mammal; (e) filling the device with a suitable amount of insulin producing cells; and (f) sealing the device to yield the insulin producing device.

DETAILED DESCRIPTION OF THE INVENTION

Figure 1:
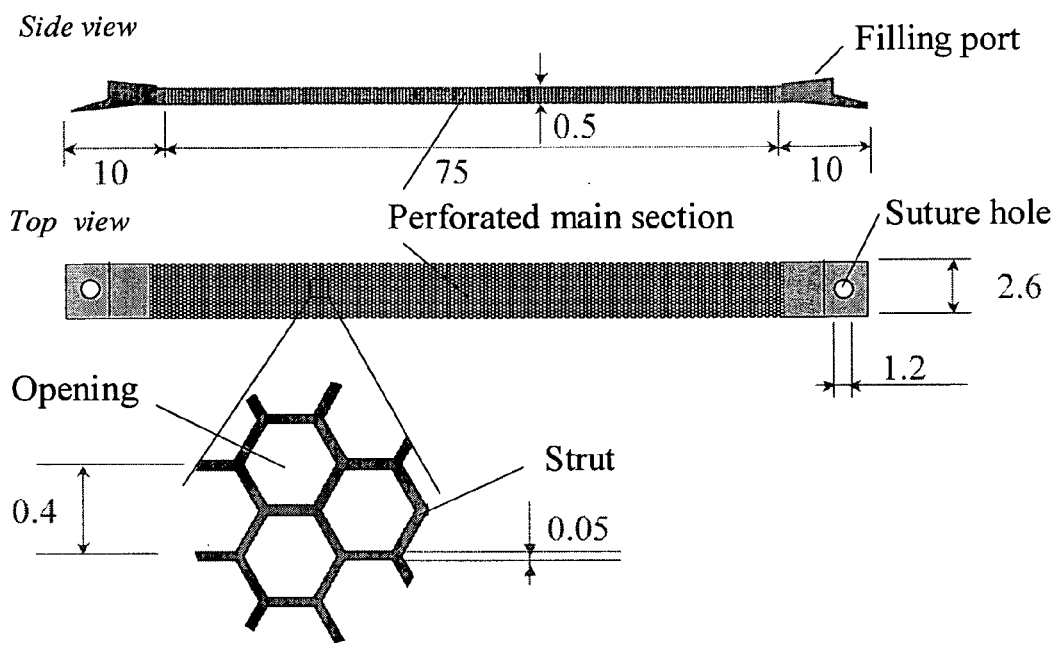
FIG. 1 is a side illustration of one embodiment of a scaffold for use in conjunction with the present invention.

The present invention generally relates to implantable devices for producing insulin in diabetic animals and to methods of making same. Some embodiments include amphiphilic biomembranes for use in biological applications (e.g., as an alternative and/or supplemental insulin source). Some embodiments also include live insulin-producing cells contained within one or more amphiphilic membranes so as to prevent or diminish an immuno-response and/or rejection by the host.

Bioartificial Pancreas (BAP):

In one embodiment, a BAP according to the present invention is designed to be implantable and explantable, and is designed to contain an appropriate number of immunoisolated porcine islets, which deliver the needed amount of insulin "on demand" to the host and thus maintains normoglycemia.

For the purposes of the present invention, it is accepted that the hypothesis, promulgated by others, that immunoisolation of living insulin-producing islets/cells by semi-permeable membranes provides a means for correcting diabetes mellitus. In order to avoid rejection, the recipient's antibodies must be prevented from becoming aware of the foreign proteins. The encapsulating material must also reliably safeguard the patient from bacteria and viruses unwittingly transferred with the animal cells. Importantly, the immunoisolatory semi-permeable membrane should allow small molecules such as oxygen, carbon dioxide, glucose and insulin to pass freely, however, should prevent the ingress of large antibodies. Studies suggest that pore diameters of approximately 30 nm can exclude the in-migration of immunoglobulins, complement, and cytokines (e.g., tumor necrosis factor) providing effective immunoisolation. A suitable membranes for immunoisolation can be formed from the networks and/or co-networks disclosed in PCT Publication No. WO 2006/073499, filed Jul. 28, 2005 and entitled "Amphiphilic Co-Networks, Films Made From Amphiphilic Co-Networks and Uses for Such Co-Networks and Films," which is incorporated by reference herein in its entirety.

In another embodiment, suitable membranes for immunoisolation can be formed from the networks and/or co-networks disclosed in PCT Publication No. WO 2008/019044, filed Aug. 3, 2007 and entitled "Amphiphilic Grafts and Co-Networks and Process for Making Same," which is incorporated by reference herein in its entirety.

In one embodiment, the present invention relies upon one or more membranes formed from the networks and/or co-networks disclosed in PCT Publication No. WO 2008/019044.

In one embodiment of the present invention, the membranes used herein are fully synthetic amphiphilic co-networks (APCNs) of co-continuous hydrophilic and hydrophobic segments with nano-architectures expressly engineered for immunoisolation. These nanoscale constructs ensure the rapid countercurrent transport of both $O_2$ and aqueous solutions (glucose, insulin, nutrients, metabolic wastes $CO_2$). Fundamentally new synthesis techniques and characterization methods are disclosed to demonstrate the novelty of the materials created. The preparative methods allow the fine tuning of various properties of the membranes and yield reproducible materials. By the use of hydrophilic and hydrophobic segments of well-defined length (molecular weight) and length-distribution (molecular weight distribution), the conduit sizes and size distributions can be controlled. The use of biocompatible moieties assures that biocompatible surfaces are obtained. The mechanical properties are controlled by synthesis parameters, etc. Special efforts were made to demonstrate the superiority of $O_2$ permeability of the membranes.

The following sections concern a description of the BAP that is designed to be filled with live porcine islets, and the preparation of the device. The BAP includes four components, all of which were specially conceived and made: The metal scaffold, the reinforcing nanomat, the immunoisolatory polymeric amphiphilic co-network (APCN) membrane, and the seals. These components were integrated into one unique device, the BAP.

Some aspects of the present invention include: (1) the synthesis of a suitable immunoisolatory membrane, or membranes, as "support means" for suitable insulin producing cells; (2) that are capable of protecting xenografts (porcine PECs) from the immune system of the host without immunosuppressive drugs; and (3) that are biocompatible and exhibit mechanical properties amenable to implantation in vivo.

Some embodiments of the present invention are capable of correcting or mitigating diabetes in mammals such as dogs or humans. In one embodiment, correction or mitigation is achieved through implantation of a bio-artificial pancreas (BAP) 100. In one embodiment, such a BAP 100 comprises an immunoisolatory device utilizing polymeric membrane 104 adapted for xeno-immunoisolation thereby enabling the encapsulation therein of insulin producing porcine endocrine cells (PEC). Thus, some embodiments relate to correcting hyperglycemia in mammals such as dogs and/or humans without immunosuppressive drugs.

The BAP 100 device can take on any of a variety of forms provided the device is capable of containing and maintaining viable islet cells while providing insulin to a host. Many embodiments include a spacing member 102, which defines the distance between two membranes 104. For example, some embodiments include a ring or washer-shaped spacing member 102 to which immunoisolatory membranes 104 can be affixed. However, in other embodiments the ring can be substituted for any appropriate shape, as long as it provides a spacing 108 between the affixed membranes 104 sufficient to provide a thickness of up to about four islet cell diameters, i.e. about 600 microns (as measured from the outer surface of one membrane to that of the other membrane). One reason for this thickness is that oxygen must diffuse into the device in order to support cellular respiration. Thus, thinner devices are expected to be operable, but cell death is expected to increase as thickness increases above 600 microns. However, operable embodiments may exist at thicknesses above 600 microns.

In some embodiments the BAP 100 (see FIG. 4) includes one or more fill ports 106, and/or vent for filling the BAP 100 device. For example, the device can include a fill port 106 that is adapted to receive a syringe needle for filling the device with islet cell culture. Such a device can also include one or more vent ports that operate in consort with the fill port, wherein displaced gases are allowed to escape through the vent as islet cells are added to the device.

In some embodiments the BAP 100 device is implanted in a diabetic host. Any of a variety of implant locations can be appropriate provided the location has sufficient blood flow and is capable of providing a sufficient means for exchanging nutrients and waste products thereby maintaining the living islet cells, and for distributing secreted insulin throughout the host's body. Some implant locations that provide such sufficient means include subcutaneous and intraperitoneal loci.

In one embodiment, the present invention utilizes a membrane 104 adapted to immunoisolate foreign cells from the immune system. In some embodiments, such immunoisolating membranes are biocompatible, biostable, non-fouling, implantable/explantable, rubbery (mechanically robust), highly $O_2$ permeable, sterilizable, soft and/or smooth. At the same time, such membranes are semi-permeable with size-controlled conduit dimensions that allow the in-diffusion of $O_2$, water, metabolites, and nutrients and the out diffusion of insulin and wastes ($CO_2$) while excluding immune cells and immunoproteins such as IgG ($M_n$=150,000 g/mole). The membranes disclosed herein meet these demanding criteria and can be synthetically tailored to the features desirable for a BAP.

Some semipermeable membranes of the present invention include amphiphilic membranes having pore size-controlled bi-continuous hydrophilic and hydrophobic domains and hydrophilic pore/channel (i.e., conduit) dimensions of about 3.0 to 4.0 nm. Some such membranes may enable survival of porcine endocrine cells (PECs) in mammals for up to three weeks or more without immunosuppression. Suitable immunoisolatory amphiphilic membranes can be synthesized from a wide variety of chemistries including various chemistries that permit the production of amphiphilic co-networks (APCNs). Suitable chemistries include, but are not limited to, those described in PCT Publication WO 2008/019044, filed Aug. 3, 2007 and entitled "Amphiphilic Grafts and Co-Networks;" and PCT Publication WO 2006/073499, filed Jul. 28, 2005 and entitled "Amphiphilic Co-Networks, Films Made From Amphiphilic Co-Networks and Uses for Such Co-Networks and Films," both of which are hereby incorporated herein by reference in their entireties.

In one embodiment, the APCN membrane comprises three components, PDMAAm (poly(N,N-dimethyl acrylamide)) and PDMS (polydimethylsiloxane) and PMHS (polymethylhydrosiloxane), which are united by a unique polymerization process to a microscopically homogeneous amphiphilic network. This network (membrane) allows the rapid simultaneous and countercurrent diffusion of hydrophilic substances (aqueous solutions) and hydrophobic molecules (oxygen).

In another embodiment, APCNs for use as immunoisolatory amphiphilic membranes can be synthesized from co-continuous covalently-linked hydrophilic poly(ethylene glycol) (PEG) and hydrophobic polydimethylsiloxane (PDMS) segments, crosslinked by tris(dimethylsilyloxy)-phenylsilane units.

Some embodiments include amphiphilic water-swollen membranes having size-controlled hydrophilic pore/channel (conduit) dimensions in the about 3.0 to 4.0 nm range. Other embodiments include immunoisolatory devices comprising the foregoing membranes, and can include bio-artificial pancreas devices. Such devices benefit from properties of membranes in accordance with the present invention including biocompatible; biostable; non-fouling; implantable/explantable; mechanically robust; highly $O_2$ permeable; sterilizable; soft and smooth. At the same time the membranes of the present invention are semi-permeable with size-controlled conduit dimensions. Thus, the membranes allow the in-diffusion of $O_2$, water, metabolites, and nutrients, and the out-diffusion of insulin and wastes (e.g., $CO_2$), but exclude immune system components, such as IgG ($M_n$=150,000 g/mole).

Some embodiments are capable of protecting xenografts (e.g. porcine PECs) from the immunoproteins of the host (e.g., dog) thereby eliminating the need for immunosuppressive drugs.

In some embodiments the membranes are biocompatible and exhibit mechanical properties that are amenable to implantation in vivo. This is accomplished by examining the tissues around the BAPs for signs of external inflammation, neo-vascularization, and fibrosis by light and electron microscopy.

Macro-encapsulation entails the protection of large numbers of cells and allows cells to be implanted and removed easily. In some embodiments macro-encapsulating membranes are biocompatible and have desirable mechanical properties that resist breakage.

Figure 20:
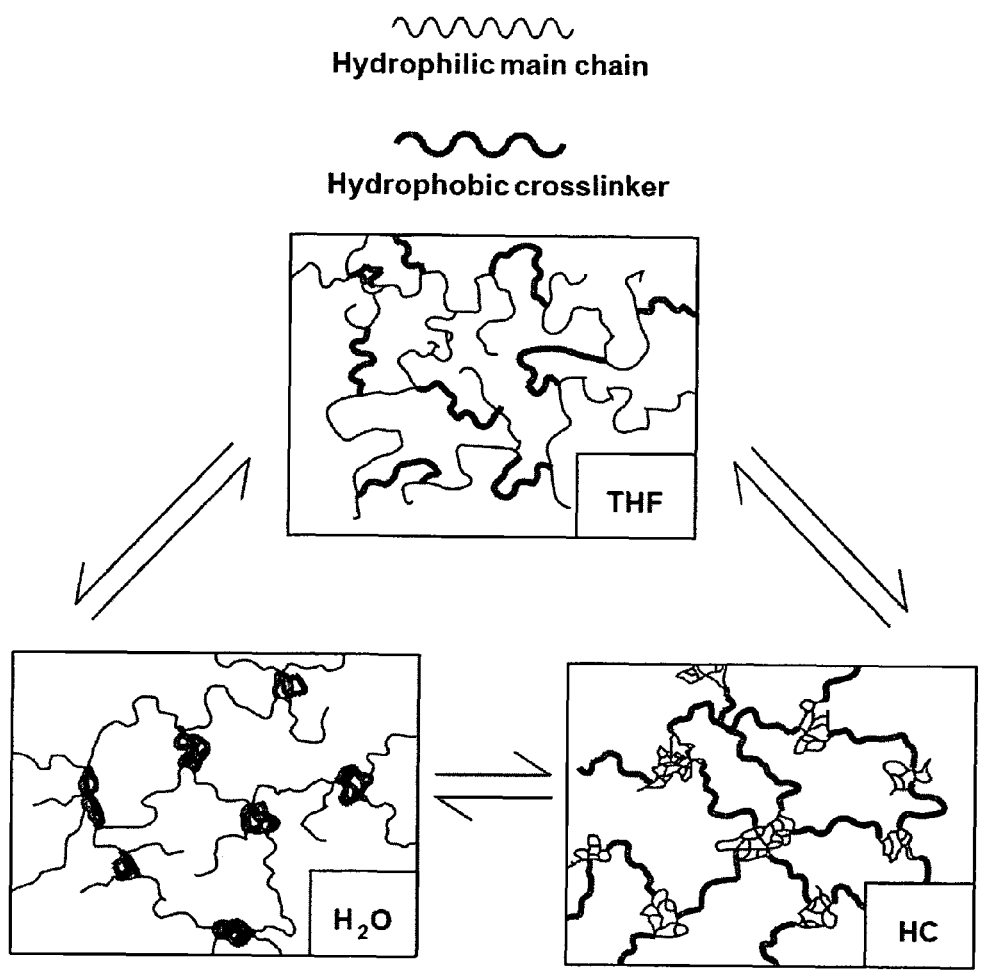
FIG. 20 is a drawing illustrating the conformational changes that the amphiphilic networks undergo in THF, hydrocarbon and water.

Amphiphilic networks (i.e., networks that contain approximately equivalent quantities of randomly crosslinked co-continuous hydrophilic and hydrophobic chain elements) which swell in water, generally have desirable mechanical properties and well-defined conduits. These networks undergo conformational rearrangements rapidly in response to a contacting medium ("smart" medium-responsive microstructures). FIG. 20 illustrates the structural rearrangements that occur rapidly and reversibly upon change of the surrounding medium from tetrahydrofuran (THF) to water ($H_2O$), to hydrocarbon (HC). While not wishing to be bound to any particular theory, this adaptation to the milieu may explain the biocompatibility of certain amphiphilic networks in accordance with one embodiment. Since amphiphilic networks in accordance with the present invention are bio- and hemo-compatible, and non-fouling in vivo they can be exploited for biological applications including, but not limited to, bio-artificial pancreases.

Amphiphilic membranes in accordance with the present invention exhibit properties that are desirable for immunoisolatory membranes. For example, some properties include (1) biocompatibility with the host (e.g., human) and guest (e.g., porcine islets); (2) hemo-compatibility; (3) bio-stability for longer than six months; (4) rapid oxygen and water transport through the membrane; (5) smooth, slippery, non-clogging, non-fouling and non-thrombogenic surfaces; (6) controlled semi-permeability: Size-controlled conduit dimensions having narrow pore-size distributions (molecular weight cutoff ranges) that allow the passage of aqueous solutions of nutrients and biologically active molecules (insulin) and the exit of metabolic wastes, but exclude immunoproteins, antibodies, and white blood cells; (7) physiologically satisfactory bidirectional fluxes of glucose, insulin, nutrients, and metabolites; (8) thin membrane walls (few micrometers) to minimize diffusion paths; (9) flexible/rubbery membranes of good mechanical properties (e.g., strength, modulus, elongation, fatigue) for the implantation and explantation of large numbers (approximately $8\times10^5$) of islets; (10) enabling all the above properties to be maintained for long periods of time (e.g., six to twelve months); (11) simple and efficient membrane synthesis; (12) easily manufactured into sealable containers (tubes, pouches, sheets) of well-defined volumes (e.g., in the 2 to 7 mL range); (13) easily implanted and explanted; (14) sterilizable; and (15) provide all of the above properties economically.

In one embodiment, the membranes of the present invention are comprised of fully synthetic polymers with nano-architectures expressly engineered for xeno-immunoisolation. In one embodiment, the membranes of the present invention are amphiphilic co-networks of co-continuous covalently-linked hydrophilic segments (e.g., poly(ethylene glycol) (PEG), certain acrylates, etc) and hydrophobic segments (e.g., polydimethylsiloxane (PDMS)). These nanoscale constructs ensure the rapid countercurrent transport of both $O_2$ and aqueous solutions (glucose, insulin, nutrients, metabolic wastes $CO_2$). The highly oxyphilic PDMS component, whose $O_2$ affinity/permeability is more than an order of magnitude larger than that of a typical hydro gel, ensures a sufficient $O_2$ supply to the encapsulated tissue.

In another embodiment, the membranes for use in conjunction with the present invention can be formed from PDMAAm, PDMS and PMHS, which are united by a unique polymerization process to a microscopically homogeneous amphiphilic network. This network (membrane) allows the rapid simultaneous and countercurrent diffusion of hydrophilic substances (aqueous solutions) and hydrophobic molecules (oxygen).

In some embodiments, properties of the membranes of the present invention can be fine-tuned. For example, conduit size and the size distribution thereof can be controlled using hydrophilic and hydrophobic segments of well-defined length (i.e. molecular weight) and length distribution (i.e., molecular weight distribution). Furthermore, mechanical properties can be controlled by manipulating synthesis parameters. Additionally, in some embodiments biocompatible surfaces can be obtained by using certain biocompatible pre-polymer species.

In one embodiment, the membranes of the present invention have superior $O_2$ permeability. In this embodiment, special efforts were made to demonstrate the superiority of $O_2$ permeability of membranes in accordance with the present invention. Indeed, the $O_2$ transparency of membranes in accordance with one embodiment of the present invention is so high that the conventional Fatt method to measure $O_2$ permeability is inadequate, and the membranes of the present invention necessitated building special equipment and developing a new methodology to quantitatively determine the $O_2$ permeabilities of the membranes of the present invention. For purposes of comparison, the $O_2$ permeability of a typical hydrogel (alginate, poly(hydroxyethyl methacrylate) soft contact lens) is 10 to 20 barrer units, while that of the present invention is in the range of about 200 to 400 barrer units. Thus, some membranes of the present invention have extremely high oxygen permeability. Specific oxygen permeabilities are controlled through composition and process conditions.

In one embodiment, the present invention entails the preparation of implantable/explantable devices for xeno-transplantation of living pancreatic porcine islets into diabetic dogs, and thus will enable the elimination and/or substantial reduction of their diabetic condition. In this embodiment, the membranes of the present invention are adapted to protect the guest tissue (healthy porcine islets) from the immune system of the diabetic host and still allow molecular communication between the islets and dog thus enabling correction of hyperglycemia without the need for immunosuppression. In one example the host animals are followed for three weeks and then the devices are removed and the blood sugar measured. The blood sugar rises following explantation, thereby demonstrating that the implanted islets are responsible for correcting the hosts' hyperglycemia.

In some embodiments, the relatively small size and high $O_2$ permeability of the membranes of the present invention permit a BAP made therefrom to be implanted intraperitoneally (IP) or subcutaneously (SQ).

Some alternative embodiments include the synthesis of amphiphilic networks containing about equal amounts of hydrophilic polyacrylates, randomly crosslinked with hydrophobic polyisobutylene (PIB) segments. The microstructure and properties of these materials have been found to have surface and mechanical properties appropriate for medical applications. In some embodiments the tensile strength equal to about 0.5 to about 3.0 MPa, and the elongation is equal to about 50 to 600%.

In one embodiment, the present invention includes amphiphilic networks prepared by free radical solution copolymerization of hydrophilic monomers [N,N-dimethyl acrylamide (DMMAAm), 2-hydroxyethyl methacrylate (HEMA), N-(dimethyl-amino)ethyl methacrylate (DMAEMA) and sulfoethylmethacrylate (SEMA)] with a hydrophobic crosslinker, methacrylate-telechelic polyisobutylenes. Further development of amphiphilic membranes has shown that they are biocompatible and non-thrombogenic. Networks containing approximately 50/50% DMAEMA/PIB ($Mn_{PIB}$=10,000 g/mole) exhibit excellent biocompatibility and stability in rats, integrate well with tissue, resist bacterial contamination, and provoke little or no fibrosis or adhesion. In cell culture and protein tests the number of cells and total protein on amphiphilic networks are similar to negative controls (polyethylene, silicone rubber, glass) indicating no toxic response. Cell adhesion and anti-adhesion experiments with human monocytes have shown inhibition of monocyte adhesion for various amphiphilic networks and glass (negative control) relative to polystyrene (positive control). Amphiphilic networks made with DMAAm or HEMA with 50% PIB have also been shown to adsorb less fibrinogen, Hageman factor, and albumin from human plasma than glass, silicone rubber or polyethylene. Together with blood counts, these data suggest that amphiphilic networks in accordance with various embodiments of the present are well accepted in vivo.

By regulating the length of $M_{c,HI}$ (i.e., the molecular weight of the hydrophilic chain segment between crosslink sites) and by the overall hydrophilic/hydrophobic composition of the membranes one can achieve semi-permeability control. The molecular weight cut off (MWCO) range (conduit size control) is a function of the length of the hydrophilic and hydrophobic segments. Thus one can tailor an amphiphilic polymer to allow the rapid countercurrent diffusion of glucose and insulin, but impede or preclude the passage of large proteins such as immunoglobulins. Systematic experimentation shows that amphiphilic membranes containing approximately 50/50 PDMAAm/PIB with $M_{c,HI}$ approximately 4500 g/mole have semi-permeability and diffusion rates suitable for immunoisolation of pancreatic islets. These membranes allow the counter-current diffusion of glucose and insulin ($M_n$ equal to 180 and 5700 g/mole, respectively) but prevent the diffusion of albumin ($M_n$ approximately 66,000 g/mole). The diffusion rates of glucose and insulin are deemed appropriate for islet isolation. Pig islets placed in such semi-permeable amphiphilic polymer tubules are viable for at least 4 months and produce insulin upon glucose challenge. Further, in one embodiment a diabetic rat fitted with a BAP containing pig islets has a reversal of diabetes without immunosuppression.

In another embodiment, the amphiphilic membranes of the present invention contain well-defined (in terms of molecular weight and molecular weight distribution) polyethylene glycol (PEG) and polydimethylsiloxane (PDMS) strands co-crosslinked by hydrosilation with one or more unique oxyphilic multifunctional siloxane crosslinking agents. Membranes formed from such combinations can allow rapid glucose and insulin transport but impedes or precludes the diffusion of IgG. These diffusion embodiments are carried out with water-swollen amphiphilic membranes by the use of fluorescent-labeled insulin and IgG. In one series of related embodiments, select membranes are first incubated with IgG for several days and subsequently used to determine glucose and insulin diffusion. The rates of glucose and insulin transport through such membranes remain unchanged, demonstrating that IgG does not clog membrane conduits.

In the same series of embodiments the rate and extent of $O_2$ diffusion through membranes formed in accordance with the present invention are so high that they could even be considered for extended-wear soft contact lens applications. In addition to optical clarity, one important parameter for this application is the highest $O_2$ permeability. The membranes of the present invention are optically clear in the dry and water-swollen state.

It is estimated that approximately 12,000 islets/kg of dog weight will be necessary to reverse the diabetic state. Therefore, some embodiments utilize approximately 132,000 islet equivalents (0.23 mL cell volume) in an approximately 11 kg dog. In some embodiments the BAP 100 is a hollow disc prepared from two approximately 50 micron thick amphiphilic membranes 104, the rims of which are glued with a silicon glue to a 0.60 mm thick stainless steel or titanium ring having a 3.1 cm aperture. FIG. 4 shows a sketch of the envisioned BAP 100. The metal ring 102 provides reinforcement/dimensional stability, x-ray contrast and acts as the spacer 108 between the two membranes 104.

While FIG. 4 details a circular embodiment, a vast number of configurations are possible. The present invention can be configured as an oval, egg-shaped, rectangle, square, triangle, pentagon, hexagon, or any other related structure.

Islet tissue can be cultured overnight in PRMI-1640 medium containing 10% fetal calf serum, 100 IU/mL of penicillin, and 100 μg/mL of streptomycin. Before loading, the BAP 100 device is sterilized by autoclaving at 120° C. for 15 minutes and allowed to cool in a tissue culture hood. The islets/cells are loaded into a syringe and injected between the two membranes 104 through a 0.4 mm wide port 106 drilled in the metal ring 102. Injection occurs under sterile conditions. After loading, the port 106 is plugged with a silicone plug, which in turn is sealed with cyanoacrylate. In this example, the volume of the device, as defined by the aperture of the ring (3.1 cm) and ring thickness (0.60 mm), is 0.46 mL. This volume is appropriate for accommodating the approximately 132,000 islets (0.23 mL volume) plus 0.23 mL of the suspending medium (alginate). The ready-to-be-used filled BAP 100 contains approximately 4.0 layers of islets. Thus, the maximum path for $O_2$ diffusion is approximately 2 islet diameters (about 300 microns).

Male 10 to 12 kg dogs are housed individually and allowed free access to dog chow and water. After a 12 hour fast, a baseline glucose tolerance test, serum C-peptide, renal function (creatinine, BUN) and liver function tests (AST, ALT, Alkaline phosphatase) is obtained. Glucose tolerance is performed by administering glucose 500 mg/kg body weight intravenously over 2 to 3 minutes. Blood glucose and insulin levels are drawn at −5, 0, 5, 10, 15, 20, 30, 45, and 60 minutes. The amount of blood required for these tests totals approximately 20 mL. Diabetes is induced by intravenous injection of alloxan (50 mg/kg) (Sigma Chemical Co. St. Louis, Mo.) and streptozotocin (STZ) (30 mg/kg) (Zanosam—obtained from the CCF pharmacy) via the cephalic vein in the foreleg. The drugs are freshly prepared aseptically as solutions, containing 100 mg/mL in trisodium citrate buffer, pH 4.5 and sterilized by filtration through 0.22 μm filters.

In one example, in vivo function of a BAP embodiment is assessed in a dog model by means of fasting blood sugars, IV glucose tolerance tests, insulin, and C-peptide levels before, after placement, and after removal of the BAP. According to this example, diabetes is chemically induced in male dogs (n=18) weighing 10 to 12 kg by a single intravenous injection of freshly prepared streptozotocin (STZ) 30 mg/kg (Zanosar) and alloxan (ALX) 50 mg/kg after a twelve hour fast. Since these drugs are known to cause hypoglycemia 8 to 16 hours after injection, the animals are kept on intravenous fluids (0.9% NaCl containing 5% dextrose) at 125 ml/hr for 24 hours. Blood glucose levels are monitored every six hours for 24 hours. Thereafter, animals are fed regular dog chow every 12 hours and receive twice daily human insulin 70/30 0.5 to 1.5 U/kg SQ (or more if glucose levels exceed 250 mg/dl) after each feeding to prevent ketosis and death. Dogs with fasting blood sugars <250 mg two weeks after chemotherapy are not utilized. Porcine C-Peptide and insulin are measured using radio-immunoassays (Linco Research, St. Charles, Mo.). The tissues around the grafts and the contents of the BAP are examined for signs of rejection (inflammatory infiltrates), neo-vascularization, cell necrosis, fibrosis, and islet cell de-granulation. No rejection occurs.

Two to four weeks after receiving STZ/ALX, the diabetes is treated with macro-encapsulated porcine cells (12,000 islets per kg). Three different polymers are used to make BAP macro-encapsulation devices. Each polymer is tested in 5 animals. For each group BAPs are implanted into an omental pouch in the peritoneum using a midline laparotomy incision under general anesthesia (see operative technique below) (N=3) or into a subcutaneous pocket created on the abdominal wall (N=2). No immunosuppression is used. Accucheck glucometers are used to monitor glucose levels daily prior to morning feeds for the first 5 days after chemotherapy and for the first five days after implantation. No exogenous insulin is administered beyond five days after implantation.

According to this example, all dogs undergo pre-operative and weekly post-operative serum C-peptide, IV glucose tolerance tests (IVGTT), insulin levels, as well as fasting blood sugars by glucometer every Monday, Wednesday, and Friday, to determine islet cell function in vivo. A complete blood count (CBC) is obtained weekly to assess inflammation. Liver function tests (i.e. alkaline phosphatase, alanine aminotransferase (ALT), and aspartate amhotransferase (AST)), renal function tests (blood urea nitrogen (BUN and creatinine (Cr)) are drawn before implantation and at three weeks to look for possible material toxicity. The BAPs are removed at 3 weeks, the dogs recover for 24 to 48 hours, and the IVGTT and insulin levels are repeated prior to euthanizing the animals with intravenous BEuthansia-D (1 mL/5 kg).

In one example each group of five animals receive the devices either intraperitoneally (IP) into omental pouches (N=3) or subcutaneously (SQ) (N=2). The high $O_2$ permeability of the BAP membranes of the present invention makes it feasible to use either site.

In one example a BAP is implanted in each of five STZ diabetic dogs and then in vivo pancreatic function (PF) tests are performed, which include IV glucose tolerance tests (IVGTT), serum insulin, and serum C-peptide. These tests are performed prior to implantation and weekly thereafter. The BAPs are removed at three weeks, and the animals are allowed to recover for one to three days. Pancreatic function (PF) is then retested to confirm that insulin and C-peptide secretion are coming from the BAP and not the native pancreas.

In a further example, the BAPs are recovered from the host and the contents thereof are tested for viable, functioning, islet cells. This can be done by immuno-staining for insulin and glucagon, and preparing slides for light microscopy to assess islet morphology and granulation. Additionally, electron microscopy can be used to assess islet cell fine structure. A test for the absence of IgG within the BAP can also be conducted to show that immuno-chemicals from the host did not penetrate the BAP.

Given the above, in one embodiment the devices of the present invention are designed to yield a novel bio-artificial pancreas (BAP) designed to correct, for example, insulin dependent diabetes mellitus (Type 1 diabetes). In one embodiment, such a BAP is implantable and explantable, and contains an appropriate number of immunoisolated porcine islets, which deliver the needed amount of insulin "on demand" and thus maintains normoglycemia.

To demonstrate the principle of operation, a BAP containing live porcine islets are assembled and implanted into pancreatomized dogs to correct their hyperglycemia. Provided these experiments by the use of the dog model are successful, the BAP can be scaled up for use in human diabetics.

The following 10 sections concern a description of the BAP to be implanted into a typical approximately 12 kg dog, together with the preparation of the device. The BAP comprises five key components: The scaffold, the reinforcing nanomat, the immunoisolatory amphiphilic co-network (APCN) membrane, the seals, and the porcine islets.

The Scaffold:

The scaffold is, in one embodiment, a perforated steel container for porcine islets that maintains a constant diffusion path between the encapsulated islets and the tissues of the host. It exhibits mechanical properties (stiffness, strength, modulus, flexibility) appropriate for manipulating the BAP during filling it with live islets, during implantation surgery, during the period of implantation in the dog (6 to 12 months), and during explantation.

FIG. 1 shows one scheme for a scaffold for use in a BAP in accordance with the present invention (dimensions are in mm). As can be seen in FIG. 1, the scaffold is a hollow ribbon (length 75, height 2.6, width 0.5 mm) of biocompatible stainless steel (315 SL), perforated with laser cut hexagonal holes (0.5 mm diagonal diameter). The width of the struts separating the holes is 0.05 mm. The volume of the scaffold is approximately about 0.28 mL (in other embodiments it can be approximately 0.4 mL) and it is designed to encapsulate approximately 120,000 islets (1000 islets/kg dog). It should be noted that the present invention is not limited to a specifically-sized BAP. Rather, the BAP of the present invention can be formed in any suitable size given the intended recipient. At the ends of the scaffold are unperforated areas each with a circular suture hole (approximately 1.2 mm diameter) for suturing the implanted BAP to adjacent tissue. Alternatively, in another embodiment, by attaching a spiral ended wire made of the same material, the surgeon can suture the device to the living tissue. The flexible nature of the connections minimizes tissue damage.

In still another embodiment, other geometric shapes can be used in addition, or in place of, the hexagonal shapes shown above. Such shapes include, but are not limited to, squares, triangles, octagons, pentagons, etc. Additionally, the features and dimensions of the scaffold are ascertained by optical microscopy (see the Quality Control section below). However, the present invention is not limited to any one size of a BAP. Rather, the size of a BAP can be modified as needed to suit the animal or person such a device would be implanted into. Another type of BAP is shown in FIG. 4.

Other materials that may be used for the scaffold are nitinol, tantalum, titanium and their alloys, or biocompatible and biostable polymeric materials sufficiently strong, stiff and elastic for the intended application. The shapes of the holes can be square or of other geometries including aperiodic penrose tile pattern that does not exhibit translational symmetry to reduce the potential kinking of the scaffold when bent. It should be noted however, that the present invention is not limited solely to the above hole geometries. Rather, any suitable hole geometry can be used in conjunction with the present invention so long as the BAP device of the present invention functions as intended/designed.

In one embodiment, the surface of the scaffold can be roughened by etching that produces micro/nano-roughness on the surface of the scaffold. Etching increases the interfacial area between the nanofibers and the exterior surface of the scaffold, and thus anchors the nanofibers through mechanical interlocking of the nanofibers and the scaffold. Several suitable methods are available for roughening and the present invention is not limited to any one such method. Chemical methods include, but are not limited to, roughening using a wide range of acids. Other suitable methods include, but are not limited to, impact roughening, such as sandblasting.

The Nanomat: Electrospinning Polyurethane:

One of the components of the BAP is the immunoisolatory membrane. The membrane is reinforced by electrospun polyurethane nanofibers. In another embodiment, other reinforcing fibers can be utilized in conjunction with the present invention. Other suitable fibers include other biocompatible polymers, other electrospinnable biocompatible polymers, or any combination thereof.

As used herein, nanofibers are fibers having an average diameter in the range of about 1 nanometer to about 25,000 nanometers (25 microns). In another embodiment, the nanofibers of the present invention are fibers having an average diameter in the range of about 1 nanometer to about 10,000 nanometers, or about 1 nanometer to about 5,000 nanometers, or about 3 nanometers to about 3,000 nanometers, or about 7 nanometers to about 1,000 nanometers, or even about 10 nanometers to about 500 nanometers. In another embodiment, the nanofibers of the present invention are fibers having an average diameter of less than 25,000 nanometers, or less than 10,000 nanometers, or even less than 5,000 nanometers. In still another embodiment, the nanofibers of the present invention are fibers having an average diameter of less than 3,000 nanometers, or less than about 1,000 nanometers, or even less than about 500 nanometers. Here, as well as elsewhere in the specification and claims, individual range limits can be combined to form additional non-stated ranges.

In another embodiment, the nanofibers may have a diameter as small as 0.3 nanometers. In yet another embodiment the nanometers have a diameter between 3 nanometers and about 25 microns. In a further embodiment, the nanofibers have a diameter of from about 100 nanometers to about 25 microns. In still another embodiment the nanofibers have a diameter of from about 100 nanometers to about a micron. Such small diameters provide a high surface area to mass ratio, such as, for example, about 300 m$^2$/g. Within the scope of the present invention, a fiber, or nanofiber, can be any length.

Thus, the preparation of the membrane starts by coating the scaffold by rotational electrospun polyurethane (PU), preferably Elast-Eon E2D, produced and sold by AorTech Biomaterials. This PU is a biocompatible and biostable elastomer with high PDMS content, high tensile strength (30 MPa) high elongation (500%) and good oxygen permeability. Electrospinning of the PU onto the scaffold covers the hexagonal holes of the scaffold with PU nanofibers (i.e., the nanomat). One reason that Elast-Eon is selected for reinforcement is that this PU contains PDMS soft segments, which mediate molecular compatibility between the APCN membrane and the reinforcing nanomat. According to the teachings of materials science, efficient reinforcement occurs only if the reinforcing agent and the matrix are molecularly compatible. Further, this elastomeric PU exhibits the required high elongation and strength of the reinforcing agent.

Besides Elast-Eon E2D, additional materials of comparable or enhanced physical and chemical properties may also be employed. These materials may include a wide range of thermoplastics and thermosets. By the use of photolytically or chemically crosslinkable moieties, additional robustness can be imparted by crosslinking the nanomat before coating it with the APCN membrane. Crosslinking helps to resist property deterioration during coating, and during use.

In another embodiment, alternative materials for the nanomat include materials containing chemical functionalities that can establish various kinds of bonding between an APCN membrane and the nanomat, e.g., hydrogen-, ionic-, or covalent-bonding at the interface between the nanomat and the APCN, and thus lead to stronger nanocomposites.

Figure 2:
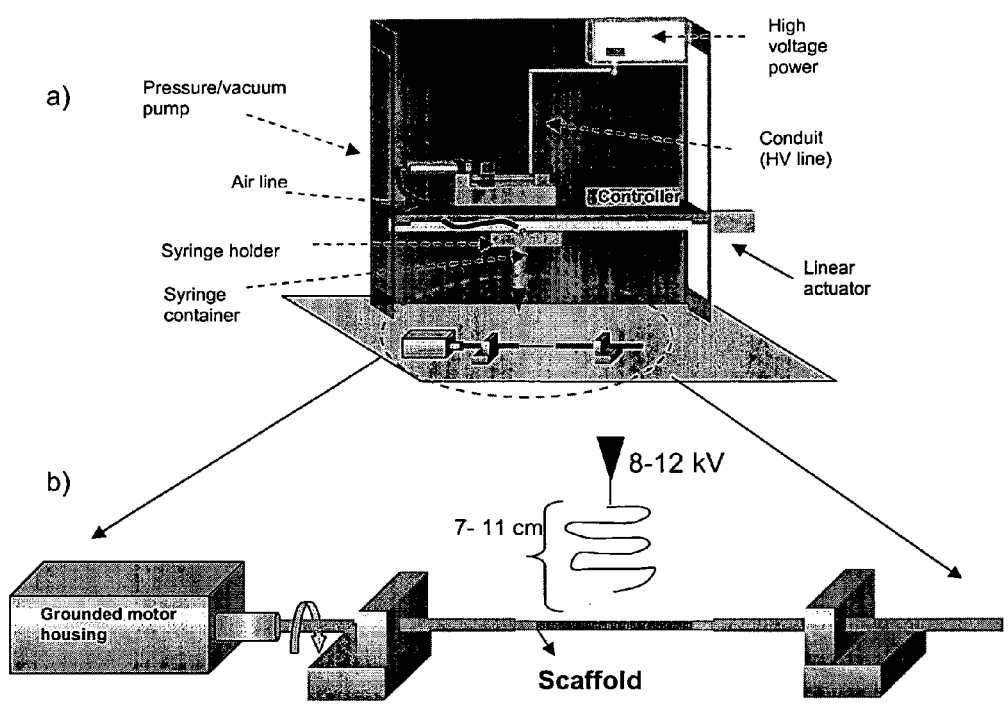
FIGS. 2(a) and 2(b) are illustrations of an apparatus for coating the scaffold by a nanomat of electrospun PU and a zoom-in image of the rotating scaffold set-up.

FIG. 2, below, shows one suitable apparatus that can be used for the preparation of the above-mentioned nanomatcoated scaffold. It should be noted that the present invention is not limited solely to the apparatus shown below. Rather, other suitable electrospinning apparatuses could be utilized herein to form the afore-mentioned nanomat. The apparatus consists of two main parts: (a) the electrospinning platform; and (b) The rotation assembly to rotate the scaffold under the spinneret.

The electrospinning platform, in its most elementary form, includes a high voltage source connected to a spinneret with a metallic needle and a ground target, which in this case is the stainless steel scaffold. One of the elements of this set-up is the linear actuator on which the spinning system is mounted. This linear actuator allows the mounted spinneret assembly to sweep the scaffold lengthwise in an oscillatory motion facilitating the uniform coating by PU nanofibers. Another element is a high precision vacuum/pressure pump to regulate the pressure levels at the tip of the metallic needle so as to prevent solution dripping onto the scaffold while electrospinning.

Figure 3:
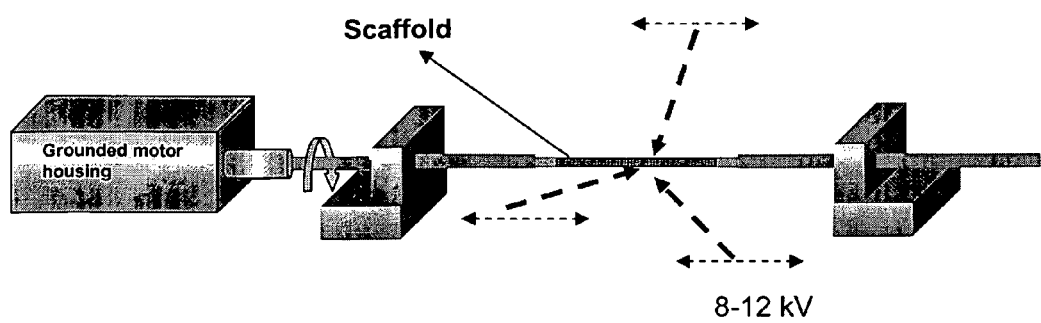
FIG. 3 is one exemplary set-up for rotating a scaffold, with such a set-up including three spinnerets.
Figure 4A:
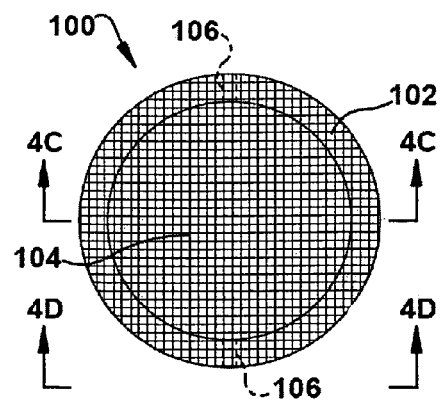
FIG. 4 is an illustration one artificial pancreas embodiment of the present invention with 4(a) detailing a top view, 4(b) detailing a cutaway top view, 4(c) detailing a cutaway side view and 4(d) detailing a side view.
Figure 4B:
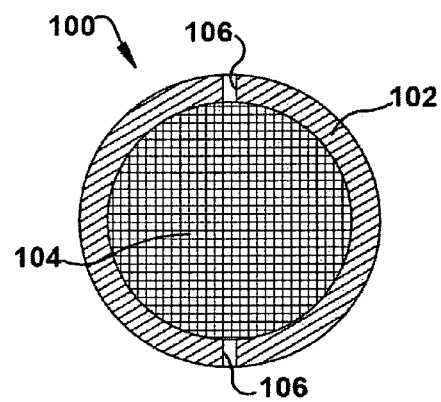
Figure 4C:
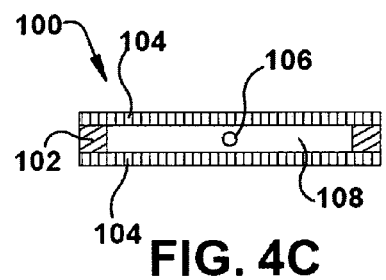
Figure 4D:
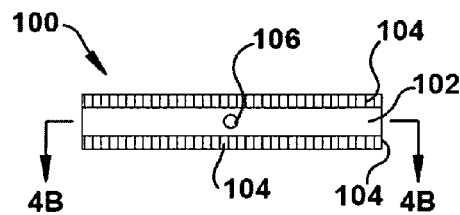

The current instrument operates with one spinneret, however the present invention is not limited thereto. Rather, any number of spinnerets can be used in conjunction with the present invention. In one embodiment, the rate of nanomat deposition can be increased by installing additional spinnerets and organizing them at an equal distance around the rotating scaffold to maximize the number of nanofibers delivered per unit time. FIG. 3 shows a rotating scaffold with three spinnerets, or three nozzles, arranged at 120° angular intervals (the dashed blue arrows depict the orientation of the nozzles). However, many more nozzles (e.g., 60) can also be employed to reduce the time of electrospinning.

The Electrospinning Solution:

A number of factors should be taken in consideration for the preparation of the electrospinning dope. First, the molecular weight of the polymer must be sufficiently high to obtain dopes with adequate viscosities for stable electrospinning. Second, conductivity plays a role in the spinability of the solution. That is, in one embodiment, it must be ensured that adequate conductivity (ionic, etc.) is present in the electrospinning dope. This can be achieved, in one instance, by the inclusion of various salts in the electrospinning dope.

In one method according to the present invention, the electrospinning solution (dope) is prepared by dissolving about 5 to about 12 weight percent Elast-Eon in N,N-dimethylformamide (DMF), or optionally in a mixture of tetrahydrofuran (THF) and DMF containing up to 50% THF. In the case of larger amounts of THF in the mixture, the evaporation rate of the solvent increases, which causes rapid solidification of the polymer at the nozzle, and the ensuing clogging may cause a halt in the electrospinning.

Figure 5:
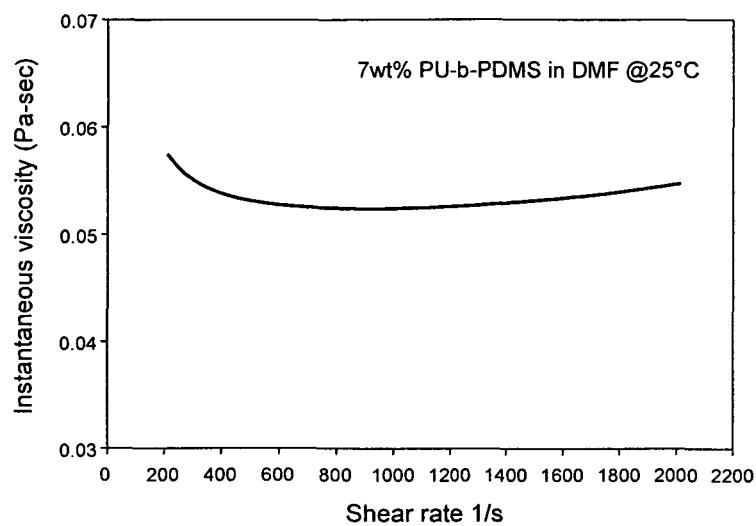
FIG. 5 is a graph of instantaneous viscosity versus shear rate of a 7 weight percent Elas-Eon in DMF solution at 25° C.

In another embodiment, 7 weight percent Elast-Eon in DMF is used for the electrospinning process. FIG. 5 shows the viscosity as a function of sheer rate of a 7 weight percent Elas-Eon in DMF solution at 25° C.

By increasing the Elast-Eon concentration from 7 to 15 weight percent in DMF, the viscosity increases dramatically (from 0.05 to approximately 3 Pa-sec), and electrospinning cannot be initiated.

Typically, the distance between the target scaffold and the tip of the needle is from about 8 to about 14 cm, and in one case about 11 cm, and the voltage levels is from about 7.5 to about 12 kV, and in one case about 9 kV.

Rotation of the Scaffold:

The scaffold is rotated continuously at about 60 to about 200 rpm to ensure uniform un-oriented fiber deposition onto the scaffold. Rates from about 3000 to about 6000 rpm could cause circumferential fiber orientation along the rotating scaffold, which reduces the permeation efficiency of the membrane. This continuous relatively slow rotation of the scaffold, along with the rasterizing (back-and-forth) motion of the linear actuator, ensures uniform coating (i.e., nanomat deposition) of the scaffold.

Nanomat Deposition Time:

A number of processing schemes can be employed to ensure strong interaction between the electrospun nanomat and the scaffold. For example, a layer of smaller diameter nanofibers can be produced by increasing the distance between the scaffold and the nozzle tip by using an a height programmable electrospinning platform. This helps to develop strong mechanical interaction between the nanomat and the scaffold. In the following stages, the height of the nozzle tip can be controlled to provide additional layers of programmed diameter nanomat.

To deposit approximately 5 mg nanofiber/nanomat uniformly onto the rotating scaffold, electrospinning is carried out for approximately 45 minutes at approximately 9 to 10 kV at a distance of approximately 11 cm from the tip of the spinneret to the scaffold. The scaffold is rotated at approximately 100 to 200 rpm and the linear actuator rasterizes the scaffold lengthwise at approximately 2 cm/sec.

Figure 6:
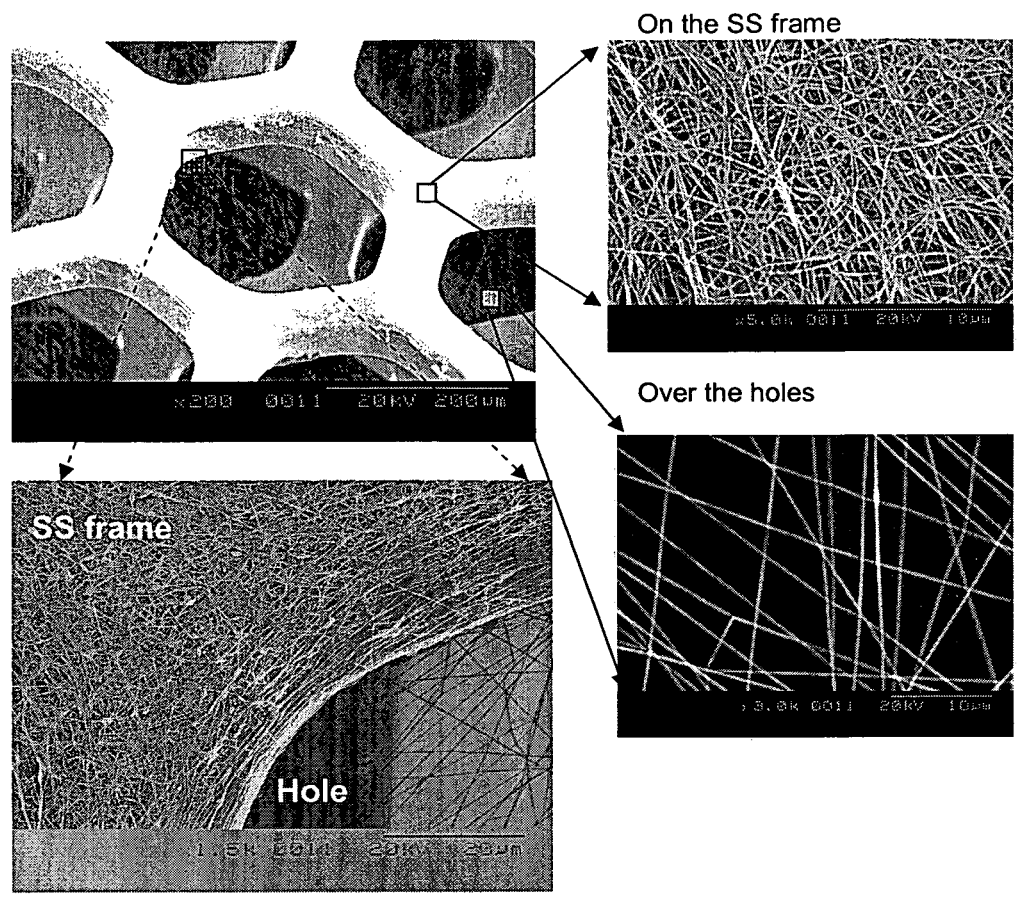
FIG. 6 is a set of photographs comparing the amount of nanofibers deposited during the first 5 minutes on the SS frame, and over the holes of the scaffold. (9 to 10 kV, 11 cm from the needle tip to the scaffold)
Figure 7:
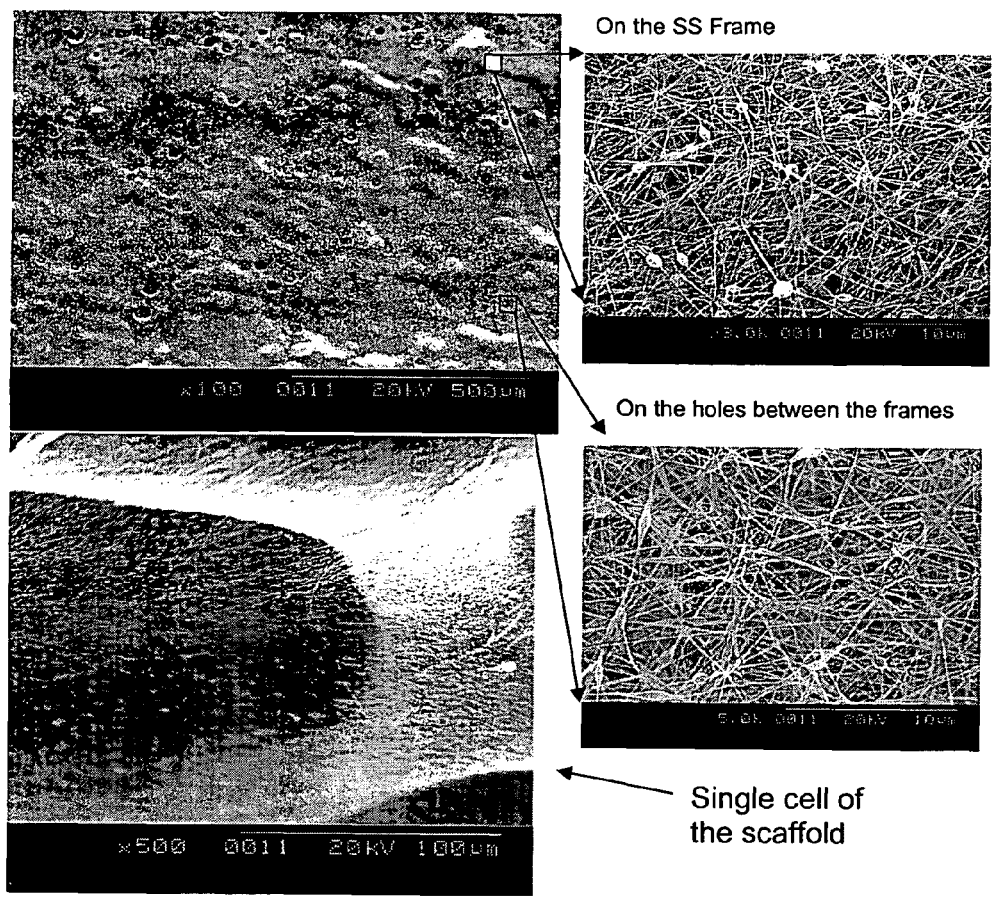
FIG. 7 is a set of photographs comparing the amount of nanofibers deposited during 30 minutes on the SS frame and over the holes of the scaffold; (9 to 10 kV, 11 cm from the needle tip to the scaffold)

Although the deposition rate of the nanomat is much faster than 0.10 mg/min, during the first 5 to 10 minutes of electrospinning the electrically charged nanofibers are preferentially attracted to the stainless steel scaffold rather than to the openings (holes). During the first approximately 5 minutes, negligible nanomat formation is observed over the holes (see FIG. 6). After sufficient fiber deposition on the stainless steel scaffold, grounding of the metal is reduced, so that nanofibers start to deposit over the holes as well, and a continuous nanomat is formed (see FIG. 7, 30 minutes image). To increase the rate of electrodeposition a conductive metal wire or ribbon is inserted into the scaffold.

The Immunoisolatory Membrane: A Nanomat Reinforced Amphiphilic Co-Network Membrane:

As is mentioned above, various types of amphiphilic networks and/or co-networks can be used to form the amphiphilic membranes of the present invention. Some exemplary amphiphilic networks and/or co-networks are discussed below. However, it should be noted that the present invention is not limited to the following examples. Rather, any suitable amphiphilic network and/or co-network can be used in conjunction with the present invention so long as such networks and/or co-networks can provide a "support means" for living insulin producing cells.

In one embodiment, suitable amphiphilic networks and/or co-networks can be found in PCT Publication No. WO 2006/073499, filed Jul. 28, 2005 and entitled "Amphiphilic Co-Networks, Films Made From Amphiphilic Co-Networks and Uses for Such Co-Networks and Films," which is incorporated by reference herein in its entirety.

In another embodiment, suitable networks and/or co-networks can be found in PCT Publication No. WO 2008/019044, filed Aug. 3, 2007 and entitled "Amphiphilic Grafts and Co-Networks and Process for Making Same," which is incorporated by reference herein in its entirety.

After the electrospinning of the PU nanomat onto the scaffold, the next step is the impregnation of the nanomat with a toluene solution of the APCN prepolymer, followed by evaporating the solvent, and crosslinking (curing) the prepolymer to the final membrane. Solvent evaporation and curing can occur simultaneously.

The preparation of the prepolymer solution for making the APCN and its crosslinking are described in detail in PCT Publication No. WO 2008/019044, and thus a detailed discussion herein is omitted for the sake of brevity. In this embodiment, the APCN comprise of three components: PDMAAm, PDMS, and PMHS, which are united by a unique polymerization process to a microscopically homogeneous amphiphilic co-network. This network (membrane) allows the rapid simultaneous and countercurrent diffusion of hydrophilic substances (aqueous solutions) and hydrophobic molecules (oxygen).

Figure 8:
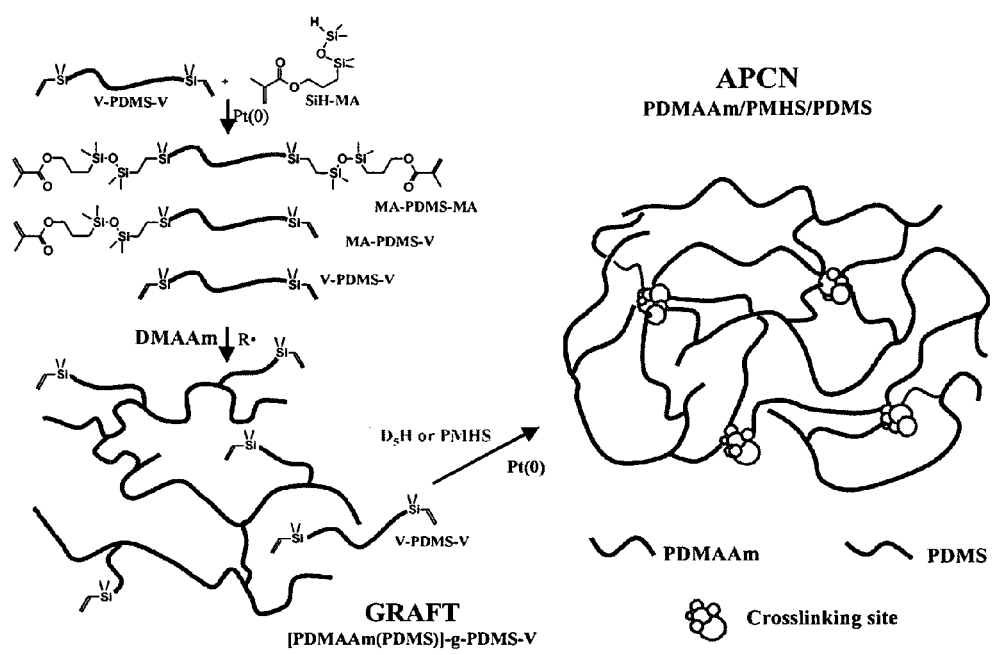
FIG. 8 is an exemplary synthesis strategy for PDMAAm/PMHMS/PDMS amphiphilic co-network membranes for use in conjunction with a BAP of the present invention.

FIG. 8 outlines the synthesis strategy for the preparation of APCN membranes, and introduces the abbreviations used.

The steps for the preparation of the APCN membrane are now briefly described. However, a more detailed explanation of this embodiment of the APCN is contained below.

Synthesis of 2-Propenoic Acid-3-(1,1,3,3-Tetramethyldisiloxanyl)propyl Ester (SiH-MA):

In a 1000 mL round bottom flask equipped with a Teflon-coated stir bar and placed in a water bath at room temperature are added tetramethyldisiloxane (134 grams, 1 mole) and allyl methacrylate (126 grams, 1 mole). The reaction is induced by the addition of Karstedt's catalyst (0.5 mL) and the charge is stirred for 3 hours. At this point triphenylphoshine (10 mL) is added and the charge is vacuum distilled (0.1 milibar) at 50° C. The product, 112 grams of a colorless liquid, is rectified on a spinning band column (75 plates, 0.3 mbar) to yield 41 g (16%) of SiH-MA, with a boiling point of 62° C.

Synthesis of V-PDMS-MA:

V-PDMS-V (20 grams, 1.4 mmol) and SiH-MA (0.37 grams, 1.4 mmol) dissolved in 23 mL toluene at room temperature are placed in a 500 mL Erlenmeyer flask equipped with a Teflon coated stir bar. The reaction is started by the addition of Karstedt's catalyst (0.02 mL Pt(0) in 3% xylene solution, and the charge is stirred and heated for two hours to 50° C. The components of the charge are not separated, and the solution of the product mixture is used as is for the preparation of grafts.

The product is analyzed by $^1$H NMR spectroscopy and GPC. The average methacrylate (MA) functionality is 1.0 (i.e., MA/PDMS=1.0). GPC analysis indicates that the molecular weight and the molecular weight distribution of the charge does not change during end functionalization.

Synthesis of [PDMAAm(PDMS)]-g-PDMS-V Graft Copolymer:

In a 1000 mL Erlenmeyer flask are placed toluene (383 mL, 340 grams), freshly distilled DMAAm (20 grams, 177 mmol), and a mixture of MA-functionalized PDMS (MA/PDMS=1.0; 20 grams in 43 mL toluene). The solution is de-aerated by bubbling Ar through it for 5 minutes, AIBN (0.3 mg, 0.18 mmol) is added, and the flask is hermetically sealed with Teflon stopcock, and placed in a heating oven for 24 hours at 65° C. After the copolymerization, the bulk of the toluene is evaporated at reduced pressure, and the product is dried in vacuum at room temperature for 2 days. The yield is 38 grams of a brittle white material.

Synthesis of PDMAAm-PMHS-PDMS Pre-Network Solution:

To [PDMAAm(PDMS)]-g-PDMS-V (0.9 grams, 0.032 mmol vinyl groups) and PMHS (0.1 gram, 0.33 mmol) dissolved in 20 g toluene is added Karstedt's catalyst (0.05 mL), and the solution is stirred at room temperature for 24 hours to form the pre-network solution. Freshly distilled toluene is added to the solution to set the concentration of the block copolymer to the range of about 6 to about 8%.

Coating the PU Nanomat with the Pre-Network Solution:

The stainless steel scaffold coated by rotational electrospinning with the PU nanomat, whose preparation is outlined above, has a silicon septum at the inlet port, and it is held at an angle of approximately 100° (from vertical). The pre-network solution, whose preparation is described above, is syringed through the silicon seal at the inlet port into the PU-coated scaffold. The advancing liquid front of the solution is constantly monitored visually, and the angle of the PU-coated scaffold is adjusted such that the advancing liquid front of the solution should increase about 0.5 to about 1 cm/sec. After the PU-coated scaffold is entirely filled with the pre-network solution, the angle of the scaffold is changed to horizontal, and the content of the device is allowed to air dry for approximately 30 seconds at room temperature. During this pre-drying step the outer surfaces of the PU-nanomat dry, and crosslinking of the pre-network solution commences; however, the interior of the device still contains liquid pre-network (toluene) solution, and both the nanomat and the membrane that is forming on the nanomat are swollen by the pre-network solution. After pre-drying, the angle of the device is changed to approximately 80° (from vertical), and the rest of the solution is removed from the device by a Pasteur pipette. The speed of the receding liquid front has to be less than about 0.5 to about 1 cm/s.

The quality of the membrane is ascertained by light microscopy (see the Quality Control section below). It is determined that: (1) the holes of the scaffold are uniformly coated with the nanomat, and that (2) the reinforcing nanomat and the APCN membrane form a homogeneous composite (i.e., the nanomat is homogeneously embedded in the membrane).

Completing the Preparation of the Immunoisolatory Membrane: Curing the APCN:

In this step the prepolymer-impregnated nanomat is cured (crosslinked) and dried, which leads to the final immunoisolatory membrane. Curing is mediated by Karstedt's catalyst dissolved in the pre-network solution. Curing starts by heating the system, continues while the toluene is evaporating, and is completed by heating for 24 hours at approximately 70° C. Curing the prepolymer yields the final membrane. Importantly, the prepolymer and the reinforcing nanomat are molecularly compatible due to the compatibilizing effect of the PDMS chains common in the APCN and the nanomat.

Extracting the Membrane:

In one embodiment, the membrane need to be extracted to prevent the release of impurities into the host during implantation. Extraction is carried out by placing the device in distilled water and gently shaking for at least one day. After water extraction the device is dried in air for 3 hours followed by drying in vacuum for 3 hours. Then the device is extracted by a 80/20 hexane/toluene mixture for 1 day to ensure that the hydrophobic extractables are also removed. To remove the toluene, the device is extracted by hexane, and finally extracted and swelled by water. The purpose of swelling in water after the hydrophobic extraction is to prevent the highly swollen membrane to shrink and fold during air-drying (shrinking/folding may cause permanent membrane damage). After the extractions, the membrane is swollen with water and then air-dried for 3 hours followed by drying in a vacuum for 24 hours at 120° C.

Sealing the Device:

The two ports of the device are sealed with a few drops of a commercially available silicon elastomer sealant (Kwik-Sil, Precision Instruments), which cures within a few minutes after the two components of the sealent are mixed. The PDMS component of the Kwik-Sil provides good adhesion to the PDMS in the APCN even in the water-swollen state. The seal exhibits high elongation (approximately 500%) and tensile strength (approximately 7 MPa), and provides excellent self-sealing plugs which can be punctured by 18, or 20, gauge syringe needles several times without compromising the seal.

Figure 9A:
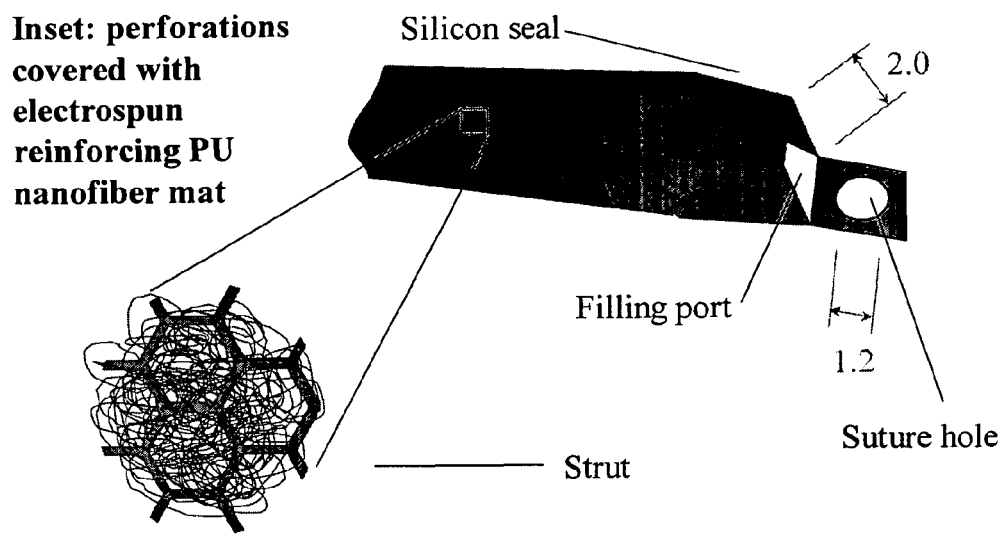
FIG. 9A is a close-up of a filling port of a device of FIG. 1 or FIG. 4 illustrating the position of the silicon seal at the port (dimensions in mm)

FIG. 9A helps to visualize the position of the silicone seal covering the ports of the device.

Quality Control:

The quality of the coated/sealed scaffold is ascertained by (A) optical microscopy and (B) burst testing.

Microscopic Examination:

After coating/sealing the scaffold is inspected by optical microscopy to ascertain: (1) the thickness of the nanomat covering the holes of the scaffold at the center of the holes and adjacent to the struts; and (2) the features, dimensions and structure (i.e., bead sizes, and bead density; entanglements and fusion junctures) of the electrospun nanofibers and nanomat.

The coated/sealed scaffold is thoroughly examined by optical microscopy for general appearance, presence of inhomogeneities, pin holes, appearance of the seals at the ports, etc. An Olympus DX51 instrument equipped with a DP70 digital camera and objective lenses with 5×, 20× and 50× magnifications can be used to provide the needed information. Experience gained in the course of examinations numerous coated/sealed scaffolds provided visuals that helped identifying unusual and/or suspicious features. Only devices judged flawless are subjected to burst testing.

Figure 10:
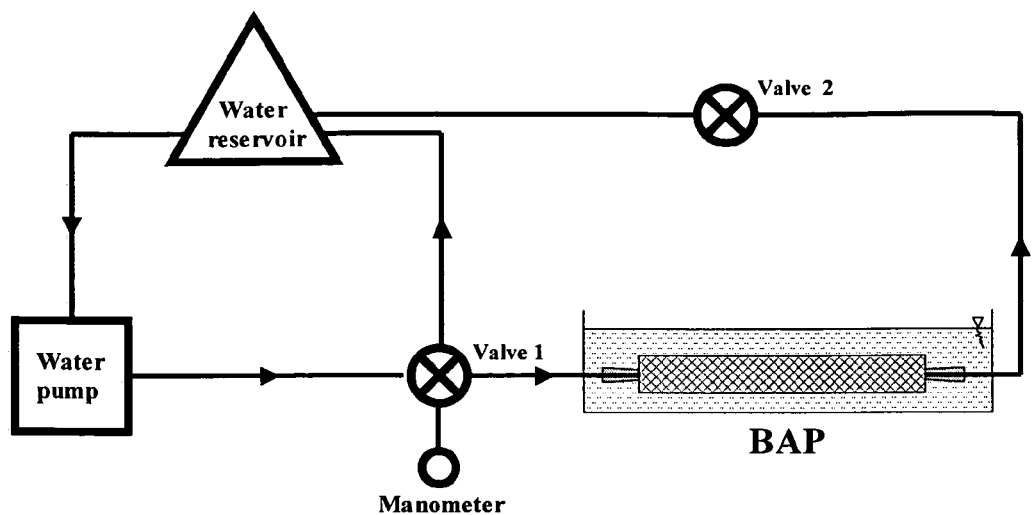
FIG. 10 is an example of a set-up designed to test the burst pressure of a BAP.

Burst Testing:

After microscopic examination, the coated/sealed scaffolds are tested for burst pressure. FIG. 10 outlines the burst pressure testing equipment.

In one embodiment, a hypodermic needle (18 gauge) is inserted into either end of the silicon rubber sealed scaffold. The inlet needle is connected to a line to a peristaltic pump delivering water to the coated/sealed scaffold, while the outlet needle is connected to a line to the water reservoir. The device is submerged in water at room temperature, and the device is flushed with water for a short period of time (approximately 1 minute). The ultimate burst pressure of a satisfactorily coated/sealed device is in the 3 to 5 psi range.

For quality control, valve 2 is closed and the pressure is slowly increased to 2 to 3 psi. When this pressure is reached, valve 1 is also closed and the pressure is monitored. A satisfactorily coated/sealed device must maintain 2 to 3 psi pressure for approximately 1 minute. Devices passing this burst pressure test are ready to be filled with islets.

Glucose and Insulin Permeation Rates:

After the preparation of prototype immunoisolatory devices (i.e., after coating scaffolds by electrospinning the polyurethane nanomat, and depositing and curing the APCN) experiments are carried out to determine the glucose and insulin permeation rates of these devices. Introductory studies reported elsewhere which concerned the effect of APCN membrane composition on permeabilities have shown that the APCN membranes having the overall composition of $PDMAAm_{61}/PMHS_6/PDMS_{33}$ (where the subscripts are weight percentages), in the absence of PU reinforcement, exhibited desirable oxygen, glucose, and insulin permeabilities, but are virtually non-permeable to albumin and IgG; therefore this APCN composition is used for the preparation of immunoisolatory devices.

Figure 9B:
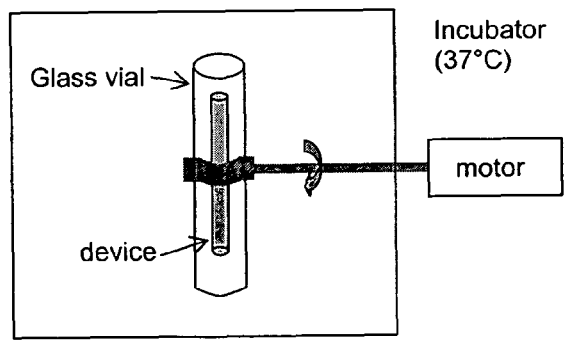
FIG. 9B is a diagram of one type of apparatus suitable to determine permeation rates.

First the scaffolds described above (length 75 mm, width 2.6 mm, depth 0.5 mm, volume approximately 100 μL) are coated by electrospinning the Elast-Eon E2D polyurethane nanomat onto the scaffold according to the method described above, and then the $PDMAAm_{61}/PMHS_6/PDMS_{33}$ membrane is deposited, cured, and extracted as is discussed above. The amount of PU nanomat deposited on the scaffold is approximately 1 mg and the amount of APCN is approximately 3 mg, i.e., the membrane contains 33% PU nanomat and 67% APCN; the thickness of the final immunoisolatory membrane is approximately 10 μm. The two ports of the scaffold are sealed per the method described above, and the device is filled by means of a 20 gauge syringe with approximately 100 μL of a 50 mg/mL glucose solution in PBS buffer, pH 7.4. Then the device with the glucose solution is placed in a cylindrical glass vial (6 mm ID×9 cm L), containing 2 to 2.2 mL PBS buffer, is placed in an incubator at 37° C., and gently agitated (tumbled). FIG. 9B helps to visualize the experimental arrangement. The glucose permeation rate of the device is obtained by withdrawing 20 μL aliquots of the PBS solution after 10 minutes, and determining the glucose concentration by the use of an Autokit Glucose™ containing glucose oxidase, and the color is read at 505 nm by a spectrophotometer (HP 845 UV/Vis).

The same sampling procedure is used to obtain insulin permeation rates. In these experiments the device is filled with approximately 0.3 mg insulin/mL of PBS containing 0.05% sodium azide to retard bacterial growth and the solutions are stabilized with 0.15% n-octyl β-D-glucopyranoside to prevent the formation of insulin aggregates. The amount of insulin that diffuses out into the PBS buffer is quantitated by withdrawing 1 mL aliquots of the PBS solution after 40 minutes; insulin concentrations are determined by the use of Bradford Reagent containing Coomassie brilliant blue G-250 dye, reading the color at 595 nm. In the presence of zinc, insulin forms dimers and hexamers:

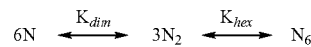

$$6N \xrightleftharpoons{K_{dim}} 3N_2 \xrightleftharpoons{K_{hex}} N_6$$

where N, $N_2$, and $N_6$ are insulin monomer, dimer, and hexamer. The equilibrium constants of dimerization and hexamerization ($K_{dim}$ and $K_{hex}$) are $6.9 \times 10^4$ 1/M and $1.3 \times 10^{13}$ 1/M², respectively. Under normal physiological conditions in live tissue, insulin is monomeric, therefore, the permeation rate of this species has to be obtained. The concentration of insulin monomer is calculated by using the equilibrium constants.

The target insulin delivery is 9.13 μg monomeric insulin/cm²·hr. To obtain this much insulin, it is assumed that the device will deliver approximately 133 μg monomeric insulin within an hour after glucose ingestion three times a day (i.e., approximately 400 μg insulin/day for a 10 kg dog), and that the total surface area of the immunoisolatory device (excluding the sealing parts) is 14.56 cm² (four 7 cm long sections of the device). Permeation experiments are performed with approximately 0.3 mg total insulin/mL PBS buffer (which is equivalent to 20.5 μg monomeric insulin/mL) in the device. The monomeric insulin concentrations are calculated from the total insulin concentrations by using the equilibrium constants shown above.

The Table A summarizes experimental results. Experiment 1 shows both the glucose and insulin permeation rates of the same immunoisolatory device; experiments 2 through 6 show either glucose or insulin permeation rates of different devices.

TABLE A

Permeation Rates of Glucose and Insulin Through Immunoisolatory Devices

| Experiment | Permeation rate of glucose (mg/cm² · hr) | Permeation rate of monomeric insulin (μg/cm² · hr) | |
|---|---|---|---|
| 1 | 11.08 | 6.81 | Average |
| 2 | | 7.61 | 8.21 |
| 3 | | 10.20 | |
| 4 | 12.12 | | |
| 5 | 7.62 | | |
| 6 | 6.85 | | |

The average permeation rate of monomeric insulin obtained by the use of three different devices is 8.21 μg/cm²·hr, i.e., a value that appears to be somewhat below the target (see above). However, the permeation rate of insulin through devices filled with islets should be higher than the data obtained because the total insulin concentration in islets is approximately 6 mg/mL (equivalent to 33 μg monomeric insulin/mL), which is significantly higher than the concentration used in the experiments. The use of approximately 6 mg insulin/mL should produce permeation rates of 27 to approximately 102 μg/cm²·hr, i.e., values significantly higher than the target insulin delivery value. Thus, it can be concluded that the insulin permeability of these immunoisolatory membranes is appropriate for a clinically acceptable BAP.

Inserting Filling- and Release-Needles into the Sealed Device:

In order to fill the device with fluid or cells, and to release the residual air and solution within the device, 18 gauge syringe needles are inserted through the seals at either ports. The needles carry adapters to accept the body of a 1 mL syringe. Care is exercised not to touch/damage the membrane during filling. The BAP is held only at the robust silicone plugs at each end or with the inserted needle. The progress of filling can be followed visually through the translucent membrane. When the BAP is completely filled with the islet suspension, first the filling needle, and subsequently the exit needle are removed.

Sterilizing:

The device with the filling- and release-needles inserted through the silicone rubber seals and filled with a phosphate buffered saline is sterilized by placing it in a tube containing the same buffer, and autoclaving by heating to 125° C. at elevated pressure for 20 minutes. The device retains its integrity through this process.

Model Experiments with Lymphocytes:

Initial experiments are performed with mouse spleenic lymphocytes as substitute representative cells for the more difficult to obtain islet cells. Freshly prepared mouse spleenic mononuclear cells are incubated overnight on tissue culture dishes to remove adherant monocytes and macrophages, are washed, and counted with Trypan blue to determine the number and percent viability of the cell population. The cells (approximately $10^8$) are then re-suspended in 0.5 mL for injection into the device. The device has an 18 gauge needle inserted into each end. A syringe is used to rinse the inside of the device with medium and then left empty. The syringe is replaced with one containing cells and the cells are injected into the device until full. The needles are removed and the filled device is incubated in growth medium in a Petri plate in a humidified incubator at 37° C. and 5% $CO_2$ (for the bicarbonate buffer system of the medium). After 3 and 7 days, the cells are expelled from the device and the number of viable cells is determined by their ability to exclude trypan blue and remain colorless.

Figure 11:
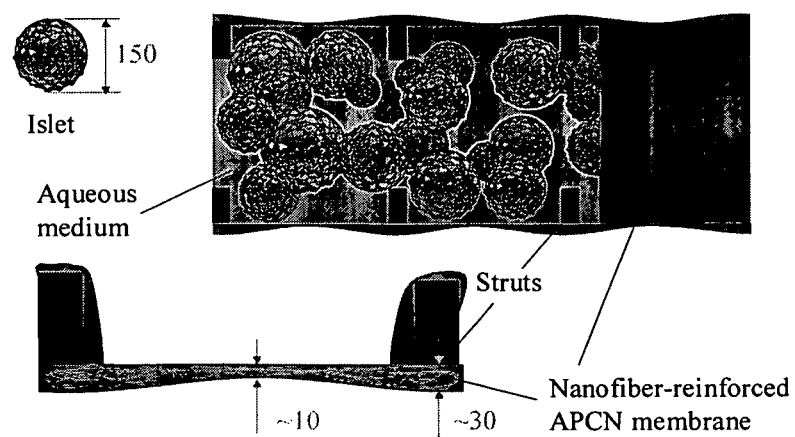
FIG. 11 is an illustration of an exemplary scheme of an islet-filled BAP in accordance with one embodiment of the present invention.

Filling the Device with Islets:

FIG. 11 helps to visualize the BAP filled with islets and ready to be implanted. The cut-away (side-view cross-section) shows randomly packed islets inside the hollow ribbon (the scaffold). The scaffold is filled with equal volumes of islets and culture medium. A 12 kg dog requires approximately 120,000 islets, i.e., 0.42 mL islet suspension (0.21 mL islet tissue plus 0.21 mL culture solution). The dimensions of the scaffold are (in mm): height 0.5, width 2.8 length 75 (total length with suture-hole platforms 95), which yields a volume of 0.105 mL; other parameters (in mm): strut height (the wall thickness of the original SS tube before perforation) 0.1, strut width 0.05, distance between adjacent struts 0.4, distance between struts on the opposite sides of the ribbon 0.3 (see FIG. 1). It is estimated that a 12 kg dog requires four such devices.

The height of the scaffold (0.5 mm) is designed to accommodate approximately 4 layers of islets. This 4-layer arrangement is a compromise between maximum blood contact and minimum size for a reasonably small device. In this arrangement the diffusion distance of oxygen to the farthest islet from blood (the oxygen source) is approximately 160 to approximately 180 microns (i.e., one islet diameter, approximately 150 microns, plus the thickness of the membrane, 10 to 30 microns). (The ideal immunoisolatory device for 120,000 islets with maximum surface area for maximum blood contact would be a approximately 150 micron diameter approximately 18 meter long tube; or a approximately 105 meter long tube for a 70 kg human; clearly unrealistic dimensions). The 4-layer arrangement with rectangular (ribbon) geometry allows the construction of a manageably small BAP.

The lower part of FIG. 11 shows the reinforced membrane between two struts. Due to the physics of electrospinning the nanomat tends to be thicker (approximately 30 microns) adjacent to the struts, and thinner (approximately 10 microns) at the center of the holes. Further, during the impregnation of the nanomat with the APCN prepolymer solution, the solution tends to accumulate around the struts. As a result of these effects the membrane exhibits a slightly undulating surface (emphasized in FIG. 11).

The suspension of islets is filled into a 1 mL plastic syringe attached to one of the needles (inlet port). Care is exercised not to touch/damage the membrane during filling, i.e., the BAP is held with two fingers at the needle. The islet suspension is pushed into the BAP very gently to minimize islet damage due to shearing. The progress of filling can be followed visually through the translucent membrane. When the BAP is completely filled with the islet suspension, first the filling needle, and subsequently the exit needle are removed. While the inlet needle is removed the device is held by the inlet seal by two fingers; similarly, while the exit needle is removed the exit seal is held by two fingers. The BAP can also be held with tweezers at the silicon plugs, or at the suture-hole platform. Contact with the membrane should be avoided to prevent damaging the membrane. Until implantation, the islet-filled BAP is hung on a hook by a suture in the suture hole, or placed into a thermostatted culture solution on a flat surface.

Alternatively, The suspension of islets is filled into a 1 mL plastic syringe and attached to one of the needles (inlet port). The islet suspension is pushed into the BAP very gently to minimize islet damage due to shearing as described above for filling the device. The progress of filling can be followed visually through the translucent membrane. When the BAP is completely filled with the islet suspension, it can be hung on a hook by a suture in the suture hole, or placed into a thermostatted culture solution on a flat surface.

Exemplary Amphiphilic Networks for Use in the Present Invention

Various types of amphiphilic networks and/or co-networks can be used to form the amphiphilic membranes of the present invention. Some exemplary amphiphilic networks and/or co-networks are discussed below. However, it should be noted that the present invention is not limited to the following examples. Rather, any suitable amphiphilic network and/or co-network can be used in conjunction with the present invention so long as such networks and/or co-networks can provide a "support means" for living insulin producing cells.

Additionally, although the examples below use $D_5H$ as a crosslinker, other suitable crosslinking compounds can be utilized. For example, PMHS can be utilized as a crosslinker.

In this embodiment, amphiphilic grafts and co-networks made from at least one hydrophilic polymer and at least one hydrophobic polymer, and to processes for preparing such amphiphilic grafts and co-networks is discussed. In another embodiment, the BAPs of the present invention utilize amphiphilic co-networks formed from the combination of at least one polysiloxane and at least one polyacrylamide. In yet another embodiment, the BAPs of the present invention utilize amphiphilic co-networks formed from the combination of at least one polysiloxane, at least one polyacrylamide and at least one crosslinking agent.

Polymers:

As is discussed above, the crosslinked amphiphilic copolymer networks or co-networks of the present invention contain at least one hydrophobic polymer and at least one hydrophilic polymer.

In one embodiment, the present invention utilizes a combination of at least one polyacrylamide (e.g., poly(N,N-dimethyl acrylamide) (PDMAAm)) with at least one di-alkenyl and/or di-alkynyl terminated siloxane polymer (e.g., polydimethylsiloxane (PDMS)) to form amphiphilic co-networks. In such an embodiment, the at least one polyacrylamide functions as the hydrophilic polymer, while the at least one di-alkenyl and/or di-alkynyl terminated polysiloxane siloxane polymer functions as the hydrophobic polymer. In one instance, each polymer used to form the amphiphilic co-networks of the present invention independently have from about 5 to about 5,000 repeating polymer units, or from about 10 to about 2,500 repeating polymer units, or from about 25 to about 1,000 repeating polymer units, or even from about 40 to about 500 repeating polymer units. Here, as well as elsewhere in the specification and claims, individual range limits may be combined.

It should be noted that the present invention is not limited to polymers having the above-mentioned number of repeating units. Instead, the present invention can utilize any suitable combination of hydrophilic and hydrophobic polymers having any number of repeating units so long as the polymers used can form amphiphilic co-networks. Another consideration that needs to be taken into account when choosing the polymers used to form the amphiphilic co-networks of the present invention is the intended use for the amphiphilic co-network. For example, if the amphiphilic co-network is going to be formed into a film to be used as a contact lens, then the polymers used in the present invention should at a minimum yield optically transparent amphiphilic co-networks. As would be apparent to one of ordinary skill in the art, depending upon the desired use for the amphiphilic co-networks of the present invention, one may have to take into consideration a wide variety of physical, chemical and/or mechanical properties of the polymers used to form such networks.

In another embodiment, the present invention utilizes a combination of at least one polydimethyl acrylamide polymer with at least one polydimethylsiloxane polymer. Exemplary acrylamide polymer (e.g., poly(N,N-dimethyl acrylamide (PDMAAm))) and polydimethylsiloxane polymers (e.g., vinyl ditelechelic polydimethylsiloxane (V-PDMS-V)) are shown below in Formulas (I) and (II), respectively,

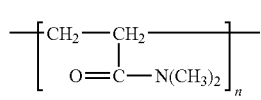

(I)

where n is equal to an integer in the range of about 5 to about 5,000, or from about 10 to about 2,500, or from about 25 to about 1,000, or even from about 40 to about 500, and

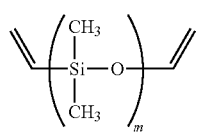

(II)

where m is equal to an integer in the range of about 5 to about 5,000, or from about 10 to about 2,500, or from about 25 to about 1,000, or even from about 40 to about 500. It should be noted that the present invention is not limited to just the acrylamide polymer and polydimethylsiloxane polymers of Formulas (I) and (II). Rather, in this embodiment any suitable combination of acrylamide polymer and di-alkenyl and/or di-alkynyl terminated polydimethylsiloxane polymers can be used.

The polydimethylsiloxane polymer of Formula (II) can also, for example, be purchased from Gelest, Tulleytown, Pa. Alternatively, if so desired, the polymers of Formulas (I) and (II) could be synthesized, thereby permitting one to control the number of repeating units present in the polymer of Formula (II).

In another embodiment, the at least one di-alkenyl and/or di-alkynyl terminated polydimethylsiloxane polymer utilized in the present invention can be selected from any polymer according to Formula (III) shown below:

(III)

where p is equal to an integer in the range of about 5 to about 5,000, or from about 10 to about 2,500, or from about 25 to about 1,000, or even from about 40 to about 500; and where $R_1$ and $R_2$ are independently $C_1$ to $C_6$ alkyl groups, or even $C_1$ to $C_4$ alkyl groups, and $R_3$ and $R_4$ are independently $C_2$ to $C_{10}$ alkenyl groups, $C_2$ to $C_7$ alkenyl groups, or even $C_2$ to $C_5$ alkenyl groups. In another embodiment, $R_3$ and $R_4$ are independently $C_2$ to $C_{10}$ alkynyl groups, $C_2$ to $C_7$ alkynyl groups, or even $C_2$ to $C_5$ alkynyl groups. Again, here, as well as elsewhere in the specification and claims, individual range limits may be combined.

In still another embodiment, $R_1$ and $R_2$ are identical substituent groups (e.g., all methyl groups, all propyl groups or all butyl groups), and $R_3$ and $R_4$ are identical substituent groups (e.g., all vinyl groups or all alkenyl groups).

Crosslinker:

In one embodiment, the present invention utilizes a silicon-containing crosslinker. Suitable silicon-containing crosslinking compositions include, but are not limited to, multi-SiH functional cyclosiloxanes. In one embodiment, the crosslinker of the present invention is or is derived from one or more alkyl-substituted cyclopentasiloxane compositions (e.g., pentamethylcyclopentasiloxane-$D_5H$). Pentamethylcyclopenta-siloxane ($D_5H$) is available commercially and its structure is shown below in Formula (IV):

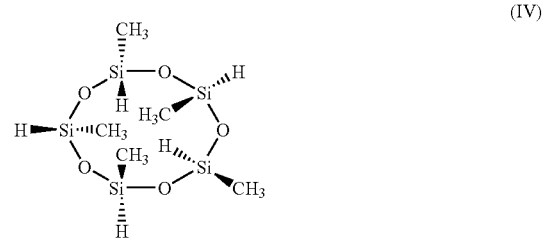

(IV)

Other crosslinking compositions in addition to the crosslinking compound shown above can be utilized in conjunction with the present invention, and the present invention is not limited to just the above crosslinking composition.

Figure 12:
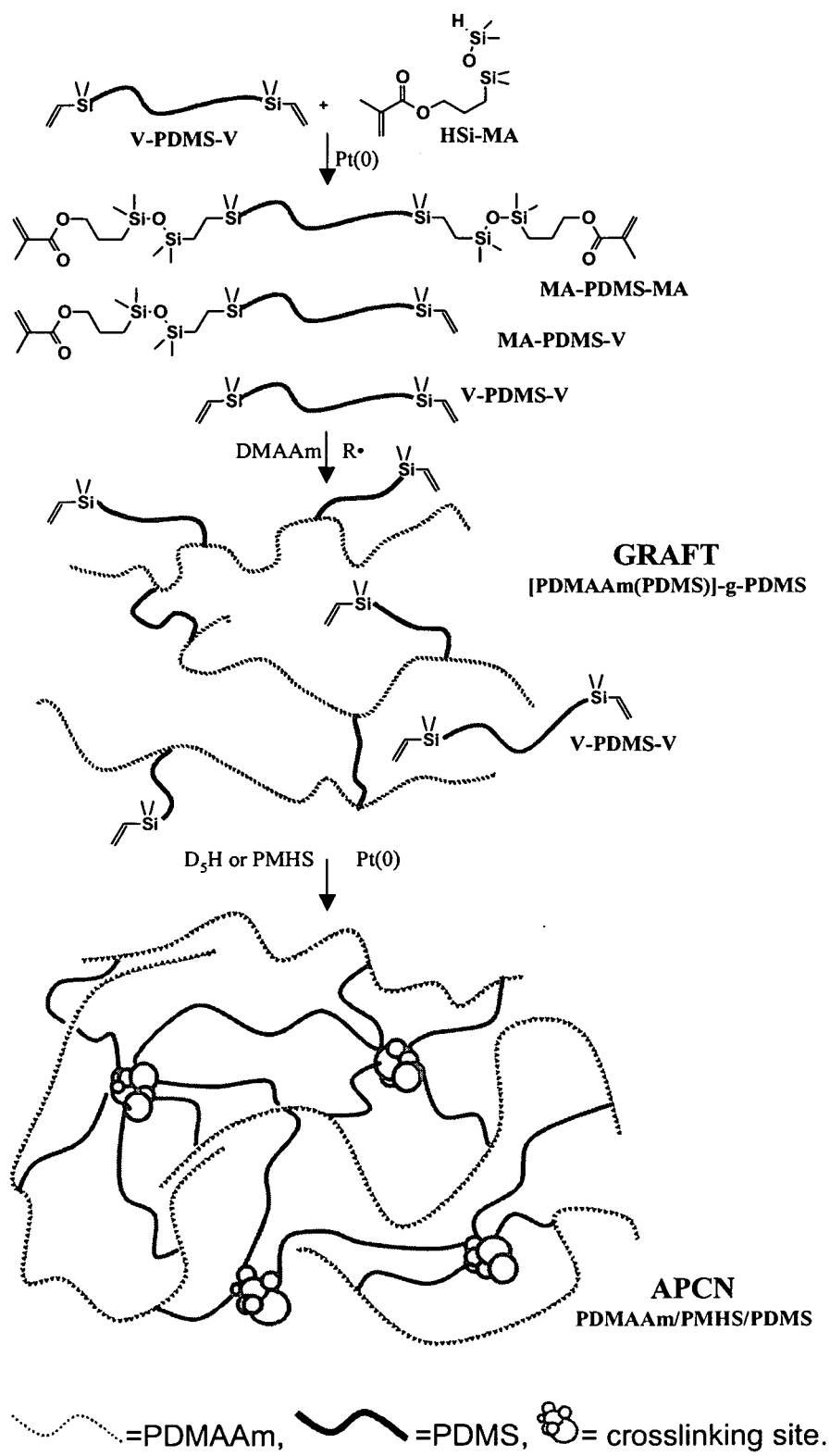
FIG. 12 is an illustration of a reaction scheme detailing the synthesis of an amphiphilic network and/or co-network according to one embodiment of the present invention; together with the abbreviations used.

Crosslinking and Formation of Amphiphilic Co-Networks:

In one embodiment, amphiphilic copolymer networks and/or co-networks are synthesized by using at least one multi-SiH functional cyclosiloxane crosslinker (e.g., $D_5H$). FIG. 12 outlines the starting ingredients for one embodiment according to the present invention, and shows an idealized structure of an amphiphilic co-network that has been crosslinked via poly-condensed $D_5H$ ($PD_5$) domains.

In this embodiment, the synthesis of an amphiphilic co-network is formed from the combination of PDMAAm, V-PDMS-V and $D_5H$ as will be explained in detail below. It should be noted that the present invention is not limited solely to this embodiment. Rather, the present invention should be broadly construed in view of the disclosure contained herein.

Materials:

Polydimethylsiloxane (V-PDMS-V, nominal $M_W$=17,000 grams/mole, provided by the supplier, $M_{n,NMR}$=14,000 grams/mole determined by the authors), tetramethyldisiloxane, pentamethylcyclopentasiloxane ($D_5H$), polymethylhydrosiloxane (PMHS, nominal $M_W$=2,000 g/mol), Karstedt's catalyst (3% Pt(0) in xylene, "low color") are purchased from Gelest, Tulleytown, Pa. N,N-dimethyl acrylamide (DMAAm), azobisisobutylonitrile (AIBN), allyl methacrylate, phosphorous acid (85%), triphenylphosphine ($PPh_3$), and the solvents tetrahydrofuran, toluene, n-hexane, and chloroform are obtained from Aldrich. PDMAAm is prepared by free radical polymerization of N,N-dimethyl acrylamide (DMAAm) in 30% toluene solution in the presence of AIBN initiator (DMAAm/AIBN=200) at 65° C.; $M_w$=80,000 grams/mole by GPC-LS.

Instrumentation:

$^1H$ NMR spectra are acquired on a Varian Unity plus 400 MHz spectrometer with the use of $CDCl_3$ solvent. GPC eluograms are obtained on a Waters GPC instrument equipped with a series of six Styragel columns (HR 0.5, HR 1, HR 3, HR 4, HR 5, and HR 6; Waters), a refractive index (RI) detector (Optilab, Wyatt Technology), a dual-ultraviolet absorbance detector (Waters 2487), a laser light scattering detector (Minidawn, Wyatt Technology) and a viscometer (Viscostar, Wyatt Technology). Samples are dissolved in THF and the flow rate is determined to be 1 mL of THF/min.

Synthesis of 2-Propenoic acid-3-(1,1,3,3-tetramethyldisiloxanyl)propyl ester (SiH-MA):

Into a 1000 mL round bottom flask, equipped with a Teflon-coated stir bar and located in a water bath at room temperature, is added tetramethyldisiloxane (134 grams, 1 mole) and allyl methacrylate (126 grams, 1 mole). A reaction is initiated by the addition of Karstedt's catalyst (0.5 mL) and the charge is stirred for 3 hours. At this point $PPh_3$ (10 mL) is added and the charge is vacuum distilled (0.1 millibar) at 50° C. The product, 112 grams of colorless liquid, is rectified on a spinning band column (75 plates, 0.3 mbar) to yield 41 grams (16%) of SiH-MA. The boiling point is determined to be 62° C.

Synthesis of MA-PDMS-V:

V-PDMS-V (20 grams, 1.4 mmoles) and SiH-MA (0.37 grams, 1.4 mmoles) dissolved in 23 mL of toluene at room temperature is placed in a 500 mL Erlenmeyer flask equipped with a Teflon coated stir bar. A reaction is initiated by the addition of Karstedt's catalyst (0.02 mL), and the charge is stirred and heated for two hours at a temperature of 50° C. The components of the charge are not separated, and the solution of the product mixture is used as is, for the preparation of grafts.

The product is then analyzed by $^1H$ NMR spectroscopy and GPC. The average methacrylate (MA) functionality is 1.0 (i.e., MA/PDMS=1.0). According to GPC analysis the overall shape of GPC traces did not change as a result of end functionalization.

Synthesis of [PDMAAm(PDMS)]-g-PDMS-V:

In a 1000 mL Erlenmeyer flask are placed toluene (383 mL, 340 grams), freshly distilled DMAAm (20 grams, 177 mmoles), and a mixture of MA-functionalized PDMS (MA/PDMS=1.0; 20 grams in 43 mL of toluene). The solution is then de-areated by sparging with Ar for 5 minutes, AIBN (0.3 mg, 0.18 mmoles) is added, the flask is then hermetically sealed with a Teflon stopcock, and placed in a heating oven for 24 hours at 65° C. After terpolymerization, the bulk of the toluene is evaporated under reduced pressure, and the product is dried, in vacuum, at room temperature for 2 days. The yield is 38 grams of a brittle white material.

Synthesis of PDMAAm/$PD_5$/PDMS and PDMAAm/PMHS/PDMS Co-Networks:

Crosslinking with $D_5H$:

Karstedt's catalyst (0.05 mL) is added to a solution of [PDMAAm(PDMS)]-g-PDMS-V (0.9 grams, 0.032 mmoles of vinyl groups) and $D_5H$ (0.1 grams, 0.33 mmoles) that is previously dissolved in 10 grams of $CHCl_3$, the resulting solution is stirred at room temperature for 24 hours. The solution is then poured into a Teflon mold (10×10 cm) and placed into an oven at 70° C. for 24 hours. After crosslinking is complete, the resulting polymer is removed from the mold, exhaustively extracted with water (3×500 mL/day) and dried, in vacuum, at room temperature. The total amount of water extractable (sol) fraction is 5% indicating a high degree of crosslinking. The product is a colorless optically clear flexible film, which can be handled manually thereby suggesting a reasonable combination of mechanical properties. The product swells both in water and n-hexane indicating APCN character.

Crosslinking with PMHS:

Crosslinking with PMHS is similar to crosslinking with $D_5H$, except PMHS (0.1 grams, 1.66 mmoles of SiH groups) are used instead of $D_5H$. The total amount of water extractable (sol) fraction is 2% indicating substantially complete crosslinking. The dry product, a transparent flexible material, swells both in water and n-hexane indicating APCN character.

Crosslinking in the Presence of Added PDMAAm:

To [PDMAAm(PDMS)]-g-PDMS-V (0.9 grams, 0.032 mmoles of vinyl groups) and PMHS (0.1 grams, 1.66 mmoles of SiH groups) dissolved in 10 grams of $CHCl_3$ are added PDMAAm ($M_w$=80,000 grams/mole, 0.05 grams) dissolved in 10 grams (11.3 mL) of THF. Then Karstedt's catalyst (0.05 mL) is added and the solution is stirred for one hour at room temperature. The charge is poured into a Teflon mold (10×10 cm) and placed into an oven for 24 hours at 70° C. After crosslinking, the polymer is removed from the mold, exhaustively extracted with water (3×500 mL/day), and dried, in vacuum, at room temperature. The total amount of water extractable (sol) is 3% indicating substantially complete crosslinking. The dry product is a white flexible material that swells both in water and n-hexane indicating APCN character.

Methods:

Swelling Measurements:

Pre-weighed samples of membranes are placed in distilled water and the extent of swelling is determined periodically by removing the membranes from the water, removing the water adsorbed to the surfaces by blotting with tissue paper, and weighing. Equilibrium water swelling ($S_w$) is recorded at room temperature when the weight of the water-swollen membranes remained unchanged for 24 hours. The following equation is used to express the data:

$$S_w = 100(m_{swollen} - m_{dry})/m_{dry}$$

where $m_{swollen}$ is the mass of the water swollen membrane and $m_{dry}$ is the mass of the dry membrane. Equilibrium water swelling of the PDMAAm domain is calculated by:

$$S_{w,PDMAAm} = 100(m_{swollen} - m_{dry} W_{PDMAAm} 0.01)/(m_{dry} W_{PDMAAm} 0.01)$$

where $W_{PDMAAm}$ is the PDMAAm content of the membrane (weight percent). The weight fraction of PDMS in the swollen state is calculated by:

$$W_{sw,PDMS}=100(m_{dry}W_{PDMS}0.01)/m_{swollen}$$

where $W_{PDMS}$ is the PDMS content of the membrane (weight percent).

Results and Discussion:

The Synthesis Strategy:

FIG. 12 helps to visualize the synthesis strategy, the starting materials, the microstructures of the products, and shows the abbreviations used. The graft is abbreviated by [PDMAAm(PDMS)]-g-PDMS-V, where (PDMS) indicates the presence of the PDMS crosslinking segments in "the backbone". The abbreviation of the amphiphilic co-network, e.g., PDMAAm/PMHS/PDMS, indicates, in sequence, the hydrophilic moiety/the crosslinking agent/the hydrophobic moiety. In one embodiment, the first step is the hydrosilation of V-PDMS-V by SiH-MA at a stoichiometric ratio of 1:1 in the presence of Karstedt's catalyst. The reaction produces a statistical three component mixture consisting of MA-PDMS-V (50%, the macro-monomer), MA-PDMS-MA (25%, the first crosslinker), and unreacted starting material V-PDMS-V (25%, the second crosslinker). In this embodiment, all three moieties are needed and will be utilized.

The second step is a free radical terpolymerization of DMAAm with MA-PDSM-V and MA-PDMS-MA to yield a high molecular weight slightly crosslinked soluble graft consisting of PDMAAm main chains carrying -PDMS-V branches. The vinylsilyl termini do not copolymerize with the MA groups therefore the product remains soluble. The terpolymerization is controlled, in this embodiment, not to reach the gel point by controlling the molecular weight of the terpolymer by adjusting the initiator (AIBN) concentration. In the third and final step, the graft is co-crosslinked to yield the target APCN by hydrosilating the pendant vinylsilane groups with the second crosslinker V-PDMS-V with a polyhydrosiloxane ($D_5H$ or PMHS). The -PDMS-V and the polyhydrosiloxane are hydrophobic, and are sequestered in the PDMS domains, therefore the solidification of the PDMAAm domains does not prevent crosslinking. The APCN is optically clear indicating the absence of massive phase coalescence. Domain aggregation during crosslinking/film casting is absent because the PDMAAm and PDMS are covalently linked already in the graft stage (see FIG. 12).

The APCN contains two kinds of PDMS strands (see FIG. 12): one that connects a PDMAAm segment with a crosslinking site, i.e., formed by crosslinking via hydrosilation of -PDMS-V branches with the polyhydrosiloxane ($D_5H$ or PMHS), and one that connects two crosslinking sites, i.e., formed by crosslinking via hydrosilation of V-PDMS-V with the polyhydrosiloxane. Thus all three components that arose in the first reaction are incorporated into the APCN and fulfill important functions.

The above-mentioned APCNs are designed with immunoisolatory membranes in mind. It has been found that swelling data is a good predictor of glucose, insulin, and oxygen permeabilities, i.e., glucose and insulin diffusivities are proportional to the volume fraction of the hydrophilic domain in the co-network and the swelling ratio of the PDMAAm ($S_{w,PDMAAm}$), and that oxygen permeability is proportional to the volume fraction of PDMS in water swollen membranes. Thus, simple swelling studies provide important guidance for optimizing synthesis conditions.

Figure 13:
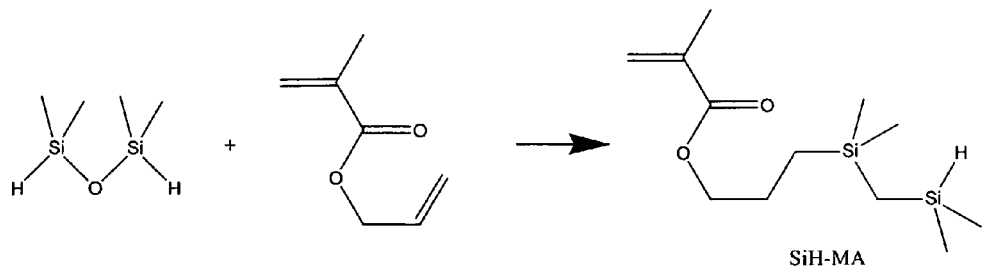
FIG. 13 illustrates the synthesis of the end-functionalizing agent SiH-MA.

The Synthesis and Characterization of the End-Functionalizing Agent, SiH-MA:

In one embodiment, the present invention begins with the synthesis of Si-MA (see FIG. 13 which illustrates the synthesis of the end-functionalizing agent SiH-MA). The function of Si-MA is to convert V-PDMS-V to PDMS with MA termini, i.e., to produce the macro-monomer MA-PDMS-V and the first crosslinker MA-PDMS-MA.

The synthesis proceeds smoothly and the product is isolated by distillation. In one embodiment, it is determined to be desirable to add $PPh_3$ to the charge prior to distillation to prevent the in-situ polymerization of SiH-MA at elevated temperatures. $PPh_3$, a catalyst poison, prevents the oxidation of SiH groups in the presence of moisture (and/or other protic contaminants) to radicals, which would mediate the polymerization of SiH-MA. In the presence of $PPh_3$ the system is sufficiently stable and gives reasonable yields of SiH-MA.

Figure 14:
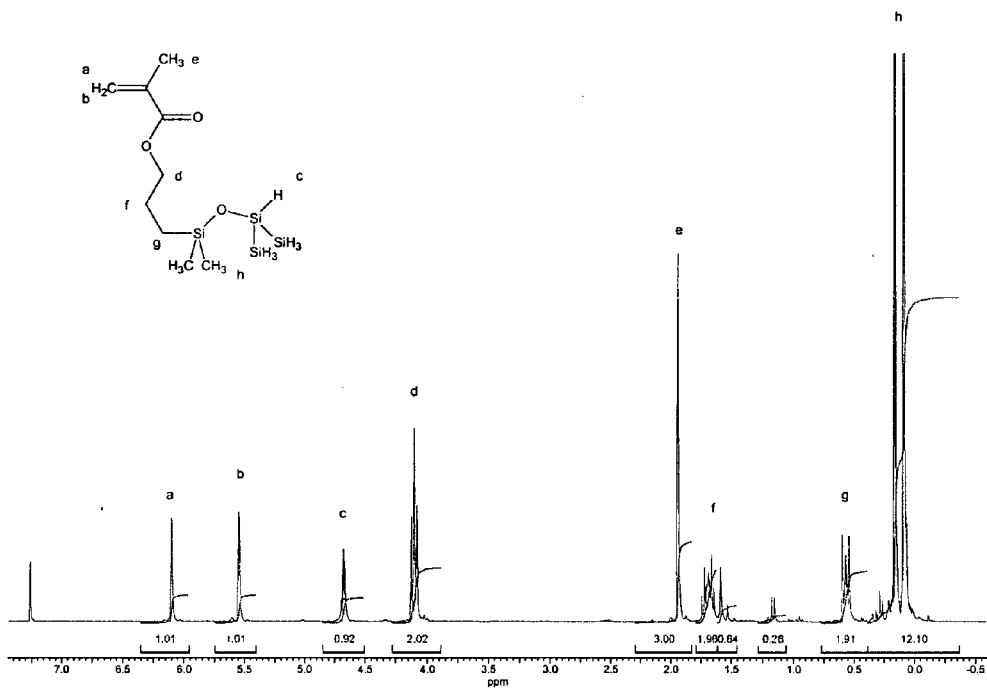
FIG. 14 is a $^1$H NMR spectrum of SiH-MA.

The structure of the SiH-MA is confirmed by $^1H$ NMR spectroscopy (see FIG. 14). As can be seen from FIG. 14 the spectra shows a multiplet at 4.67 ppm which indicates the presence of the SiH group, and characteristic resonances at 1.9, 5.6 ppm (for the olefinic) and 6.2 ppm (for the methyl protons), associated with the MA group. SiH-MA was virtually quantitatively combined with V-PDMS-V by hydrosilation, and thus PDMS with MA termini was obtained (see below).

The Synthesis of MA-PDMS-V:

The macromonomer MA-PDMS-V is prepared by hydrosilation of V-PDMS-V with SiH-MA using stoichiometric quantities of the starting materials, V-PDMS-V:SiH-MA=1:1. The product is a statistical mixture of MA-PDMS-MA (25%), MA-PDMS-V (50%), and unreacted V-PDMS-V (25%) (See step one in FIG. 12).

Figure 15:
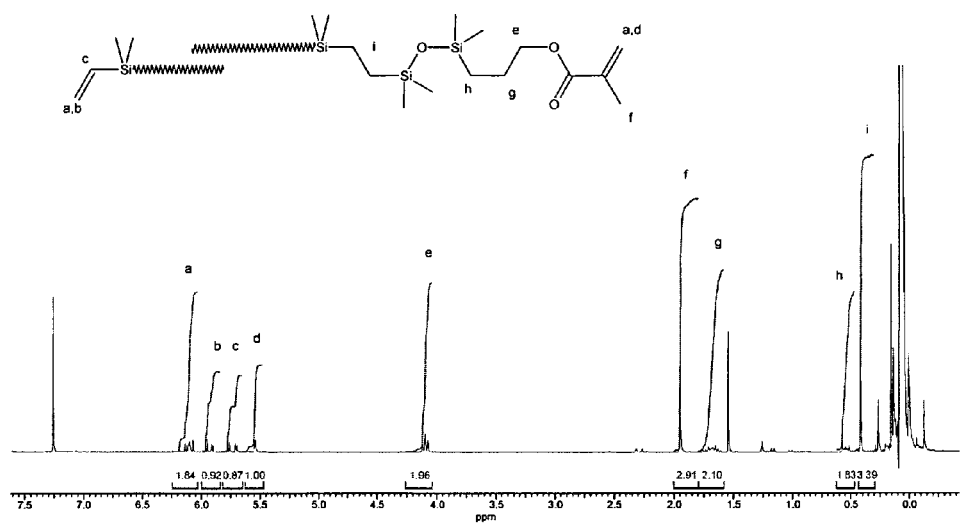
FIG. 15 is a $^1$H NMR spectrum of a product mixture according to the present invention.

FIG. 15 shows the $^1H$ NMR spectrum of the mixture, and shows resonances characteristic of both methacrylate (a, d and f protons) and vinylsilyl (a, b and c protons) groups. The resonances associated with the SiH proton (4.67 ppm) have completely disappeared. The resonance for the $CH_2$ protons, which arose via hydrosilation of Si—CH═$CH_2$ by SiH-MA, appear at 0.4 ppm (i protons).

The main product, MA-PDMS-V is in fact a macromonomer, whose MA group copolymerizes with DMAAm (see Step 2 in FIG. 12), and yields a graft with -PDMS-V branches. The vinylsilyl termini are un-reactive with MA under free radical conditions, however, they are needed for crosslinking by hydrosilation (see Step 3 in FIG. 12).

The reaction mixture is used as is, i.e., without separating the individual molecules, to prepare a high molecular weight graft fitted with —Si—CH═$CH_2$ groups (see graft in FIG. 12). In one embodiment, the syntheses of grafts using charges with V-PDMS-V/SiH-MA stoichiometries below or above unity (i.e., with 0.5, 0.8, 1.5) yields products unsatisfactory for some applications as the products are, for example, opaque, microphase separated grafts, or have insoluble fractions.

The Synthesis of the Graft [PDMAAm(PDMS)]-g-PDSM-V:

The synthesis of this graft entails the free radical mediated terpolymerization of DMAAm with the MA-PDMS-V macromonomer and the MA-PDMS-MA crosslinker, and yields a high molecular weight graft consisting of PDMAAm main chains carrying -PDMS-V branches slightly crosslinked with PDMS segments. Due to the presence of MA-PDMS-MA in the charge (see Step 2 in FIG. 12) the graft is slightly crosslinked and of high molecular weight. The MA-PDMS-MA copolymerizes with DMAAm, and it beneficially increases the molecular weight and broadens the molecular weight distribution of the graft. The vinylsilyl groups in V-PDMS-V do not copolymerize with methacrylates under free radical conditions. The unreacted starting material V-PDMS-V "takes a ride" and will be incorporated into the target co-network during crosslinking (see Step 3 in FIG. 12). FIG. 12 shows an idealized micro-architecture of a graft; the presence of the unreacted V-PDMS-V is indicated adjacent to the graft.

Since the copolymerization is stopped before the gel point, the product is soluble and, after drying, can be re-dissolved in various solvents (toluene, chloroform, tetrahydrofuran, etc.). Let it be stressed that although the charge contained approximately 25% MA-PDMS-MA, the graft did not contain gel because the molecular weight of the main chain was controlled by the initiator (AIBN) concentration. Relatively high initiator concentrations decrease molecular weights, while lower initiator concentrations lead to relatively higher molecular weights. Depending on the molecular weight and overall composition, the product is a colorless rigid or waxy, and opaque or optically clear material.

The molecular weight of the graft strongly affects the properties of the target co-network. In one embodiment, low molecular weight grafts lead to many dangling PDMAAm chain ends in the final co-network; the dangling ends increase water swelling and thus desirably increase aqueous diffusion, however, they weaken the co-network on account of reduced crosslink densities.

Figure 16:
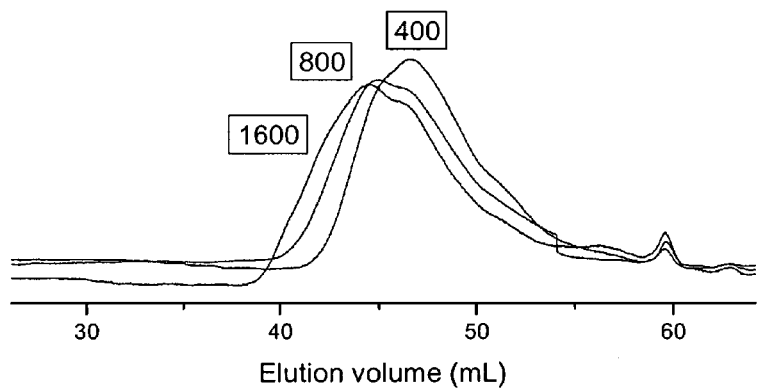
FIG. 16 is a graph of GPC traces of representative [PD-MAAm(PDMS)]-g-PDMS-V grafts prepared with different DMAAm:AIBN ratios (400, 800 and 1600)

FIG. 16 shows the GPC traces of the three representative grafts prepared with different AIBN concentrations. The traces suggest high molecular weight somewhat heterogeneous products, which is not surprising in view of the complexity of the terpolymerization. The position of the main elution peaks of the grafts shift to lower elution volumes with decreasing AIBN concentrations. High molecular weight soluble grafts can be formed, in one embodiment, only if the average arm number of the graft is in the 2 to 5 range. If the arm number is less than two, networks cannot form, and if it is larger than five, the graft contains gel. Since the molecular weight of the PDMS branch is the same in all charges (17,000 grams/mole), the molecular weight of the PDMAAm needs to be decreased to keep the arm number in the desirable range.

Figure 17:
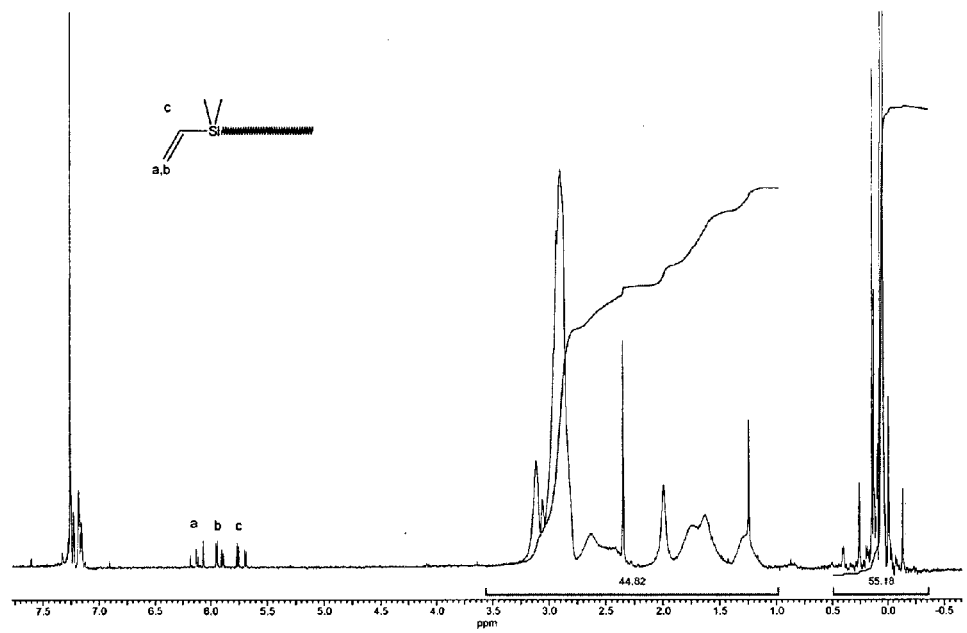
FIG. 17 is a $^1$H NMR spectrum of a [PDMAAm(PDMS)]-g-PDMS-V (sample 35-400 in Table 1)

FIG. 17 shows the $^1$H NMR spectra of a representative graft. The spectrum of FIG. 17 indicates the presence of 0.036 mmoles vinylsilyl groups/g product (calculated from the ratio of PDMS protons at 0 ppm and vinylsilyl protons at 5.5 to 6.5 ppm). The absence of MA groups indicates their substantially complete conversion.

Crosslinking the Graft to Amphiphilic Co-Network (APCN):

The target APCN is obtained by co-crosslinking the -PDMS-V branches of the graft and V-PDMS-V with polyhydrosiloxanes, $D_5H$ or PMHS, in the presence of a platinum (Pt) catalyst.

Figure 18:
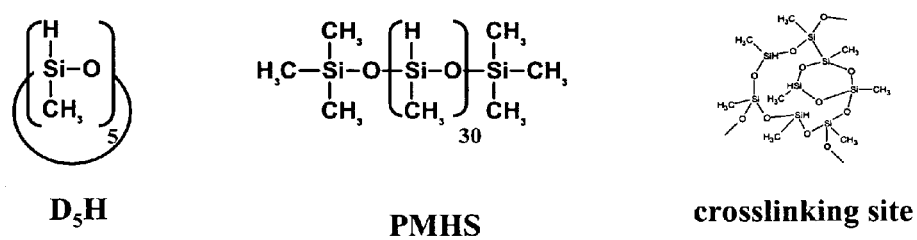
FIG. 18 are chemical formulas of select components utilized in one embodiment of the present invention.

While not wishing to be bound to any one theory, it is believed that the crosslinking sites in these APCNs arise by co-hydrosilation of PDMS-V branches and V-PDMS-V by polyhydrosiloxanes ($D_5H$ or PMHS) in the presence of Karstedt's catalyst and traces of moisture. Since the structures of $D_5H$ and PMHS are similar, and since crosslinking by hydrosilation/condensation with these crosslinkers is similar, the crosslinking sites that arise from these crosslinkers are also believed to be similar. FIG. 18 shows the structures of $D_5H$ and PMHS, and an idealized structure of a crosslinking site in the present invention's APCNs, i.e., a complex system of condensed silsesquioxane rings similar to the microstructure of $PD_5$. The ring clusters shown in FIG. 12 symbolize these complex crosslinking sites.

The graft, the crosslinker ($D_5H$ or PMHS), and the catalyst are soluble in toluene, and crosslinking by casting these solutions onto various surfaces (Teflon, glass, stainless steel) produces colorless optically clear membranes. FIG. 12 shows an idealized microstructure of an APCN.

Crosslinking accelerates during solvent evaporation because the concentration of the chain ends increases. Eventually a phase-separated product is formed, however, crosslinking continues within the hydrophobic (PDMS) domains. Since both the vinylsilyl and the SiH groups are connected to hydrophobic chains and therefore are sequestered within the rubbery PDMS domains, solidification of the separate glassy PDMAAm domains during crosslinking does not prevent hydrosilation. Crosslinking occurs below the $T_g$

TABLE 1

Charges[a] and Overall Graft Compositions

| Graft designation | MA-PDMS-V MA-PDMS-MA V-PDMS-V (g) | DMAAm (g) | DMAAm/AIBN (mol/mol) | PDMAAm in the graft (wt %) | Elution volume of main peak (mL) |
|---|---|---|---|---|---|
| 20[b]-200[c] | 4 | 16 | 200 | 20 | 42.9 |
| 35-400 | 7 | 13 | 400 | 35 | 41.4 |
| 50-400 | 10 | 10 | 400 | 50 | 44.4 |
| 50-800 | 10 | 10 | 800 | 50 | |
| 50-1600 | 10 | 10 | 1600 | 50 | 42.9 |

[a]All charges contained 180 g toluene;
[b]PDMAAm content of the graft, and
[c]DMAAm/AIBN ratio Table 1 summarizes the amount in grams of the charges, the amount in grams of DMAAm added to the charges, the ratio in mol/mol of DMAAm/AIBN, the weight percent of PDMAAm in the graft, and the elution volume in mL of the main GPC peak. According to the last parameter, the molecular weights of the grafts are high (above 100,000 grams/mole, as estimated by polystyrene calibration). Since the relative amounts of PDMAAm and PDMS are not constant, and the product is branched, accurate molecular weight cannot be determined by GPC.

of the PDMAAm phase ($T_g=114°$ C.) and the overall morphology of the APCN changes constantly during curing, as indicated by the originally opaque/white films turning gradually optically clear. The optical clarity of the membranes both in the dry or wet sate suggests domain dimensions well below the wavelength of visible light, most likely in the 10 to 40 nm range. Indeed, massive phase coalescence and/or domain aggregation cannot occur during crosslinking/casting because the PDMAAm and PDMS segments are covalently connected already in the graft.

Since the rate of crosslinking with $D_5H$ is relatively slow (minutes to hours) and is relatively sensitive to conditions leading to appropriate swelling characteristics. Swelling data are important guidance to the ultimate membrane properties.

TABLE 2

Charges, Compositions, and Swelling of APCNs

| Sample[a] | APCN Charges | | | | | | | | Properties | | |
|---|---|---|---|---|---|---|---|---|---|---|---|
| | Graft | | Crosslinker | | | PDMAAm Homopolymer | | Sol | | | |
| | Code | Conc. (wt %) | Charge (mg) | $D_5H$ (wt %) | PMHS (wt %) | Charge (mg) | Conc. (wt %) | Charge (mg) | Fraction (wt %) | $S_w$ (%) | $S_{w,\,PDMAAm}$ (%) | $W_{sw,\,PDMS}$ (%) |
| Composition of the Co-Network | | | | | | | | | | | | |
| PDMAAm$_{18}$/PMHS$_{10}$/PDMS$_{72}$ | G20-200 | 90 | 450 | 0 | 10 | 50 | 0 | 0 | 5.3 | 18 | 67 | 73 |
| PDMAAm$_{32}$/PMHS$_{10}$/PDMS$_{59}$ | G35-400 | 90 | 450 | 0 | 10 | 50 | 0 | 0 | 3.2 | 33 | 105 | 52 |
| PDMAAm$_{45}$/PMHS$_{10}$/PDMS$_{45}$ | G50-1600 | 90 | 450 | 0 | 10 | 50 | 0 | 0 | 2.7 | 60 | 133 | 34 |
| Effect of Crosslinker Concentration | | | | | | | | | | | | |
| PDMAAm$_{48}$/PMHS$_{14}$/PDMS$_{48}$ | G50-1600 | 96 | 480 | 0 | 4 | 20 | 0 | 0 | 9 | 89 | 185 | 28 |
| PDMAAm$_{47}$/PMHS$_{7}$/PDMS$_{48}$ | G50-1600 | 93 | 465 | 0 | 7 | 35 | 0 | 0 | 4.3 | 67 | 149 | 33 |
| PDMAAm$_{45}$/PMHS$_{10}$/PDMS$_{45}$ | G50-1600 | 90 | 450 | 0 | 10 | 50 | 0 | 0 | 2.7 | 60 | 133 | 34 |
| PDMAAm$_{43}$/PMHS$_{15}$/PDMS$_{42}$ | G50-1600 | 85 | 425 | 0 | 15 | 75 | 0 | 0 | 5.3 | 73 | 152 | 30 |
| Effect of the Molecular Weight of the [PDMAAm(PDMS)]-g-PDMS Graft Copolymer | | | | | | | | | | | | |
| PDMAAm$_{45}$/PMHS$_{4}$/PDMS$_{51}$ | G50-400 | 90 | 450 | 0 | 10 | 50 | 0 | 0 | | 97 | 215 | 28 |
| PDMAAm$_{45}$/PMHS$_{4}$/PDMS$_{51}$ | G50-800 | 90 | 450 | 0 | 10 | 50 | 0 | 0 | | | | |
| PDMAAm$_{45}$/PMHS$_{4}$/PDMS$_{51}$ | G50-1600 | 90 | 450 | 0 | 10 | 50 | 0 | 0 | 2.7 | 60 | 133 | 34 |
| Morphology Modification of APCNs by Blending and Extraction of Homo-PDMAAm | | | | | | | | | | | | |
| PDMAAm$_{48}$/D$_5$H$_4$/PDMS$_{48}$ | G50-800 | 90 | 480 | 4.3 | 0 | 20 | 0 | 0 | 7.2 | 92 | 190 | 27 |
| PDMAAm$_{48}$/D$_5$H$_4$/PDMS$_{48}$ | G50-800 | 90.9 | 480 | 4.0 | 0 | 20 | 5.1 | 25 | 13 | 155 | 320 | 20 |
| PDMAAm$_{48}$/D$_5$H$_4$/PDMS$_{48}$ | G50-800 | 86.5 | 480 | 3.8 | 0 | 20 | 9.6 | 50 | 19 | 220 | 460 | 16 |
| PDMAAm$_{48}$/D$_5$H$_4$/PDMS$_{48}$ | G50-800 | 78.9 | 480 | 3.5 | 0 | 20 | 17.5 | 100 | 25 | 300 | 620 | 13 |
| PDMAAm$_{48}$/D$_5$H$_4$/PDMS$_{48}$ | G50-800 | 69.8 | 480 | 3.1 | 0 | 20 | 27.1 | 175 | 42 | 380 | 790 | 11 |

[a]The numbers in the sample indicate the final composition of the APCN.

(i.e., moisture content, nature of the solvent, solvent evaporation rate, time before casting, etc.), experiments were preferentially carried out with PMHS which provides faster and more reproducible crosslinking. The repeat units of these polyhydrosiloxanes are identical, —SiH(CH$_3$)—O—, except $D_5H$ is cyclic whereas PMHS is linear, and it contains about six times as many SiH groups per molecule as $D_5H$ (see FIG. 18). Indeed crosslinking was much faster and much less sensitive to solvent related issues with PMHS than with $D_5H$.

In view of the great structural similarity of $D_5H$ and PMHS, the gross structures of the crosslinking sites formed from these moieties are expected to be similar. Since $D_5H$ and PMHS contain the same repeat units, thus the chemical transformations, which occur during crosslinking with these polyhydrosiloxanes, are expected to produce similar crosslinking sites, i.e., mixtures of different sized polysiloxane/silsesquioxane rings (indicated in FIG. 12).

Table 2 summarizes experiments carried out to explore synthesis conditions, specifically, to investigate conditions Experimentation is carried out to determine the optimum molecular weight of the PDMS segments. Thus APCNs are prepared using 9,000, 17,000, and 26,000 grams/mole V-PDMS-V. It is determined that 9,000 and 26,000 grams/mole V-PDMS-V inefficiently crosslinks and yields products of poor mechanical properties (rigid products and macrophase separation, respectively). Membranes that are prepared with 17,000 grams/mole V-PDMS-V give the best overall properties and efficient syntheses.

Composition of the Co-Network:

It is known in the art that the equilibrium water swelling of APCNs is affected by the hydrophilic polymer content. At lower hydrophilic contents (10-30%) water swelling increases are usually more pronounced than at higher hydrophilic contents (>40%) where the swelling ratio increase is directly proportional to the composition, i.e., the swelling ratio of the hydrophilic domain reaches a limiting value. While not wishing to be bound to any one theory, it is determined that the water swelling ratios of membranes according to the present invention seem to comply to this general rule since the equilibrium water swelling of the PDMAAm domain increased only 30% (from 104% to 133%) as the PDMAAm content of the co-network is increased from 31.5% to 45% (see the data contained in Table 2). These swelling results indicate that by increasing the PDMAAm content of the co-networks only a very limited improvement can be made in terms of diffusion properties (by the increase in the volume fraction of the hydrophilic channels which is already at 66%, in the case of the 50-H network), and such an increase would yield a significant decrease in the PDMS volume fraction (already at 34%, in the case of the 50-H network) which would severely decrease oxygen permeability.

Figure 19:
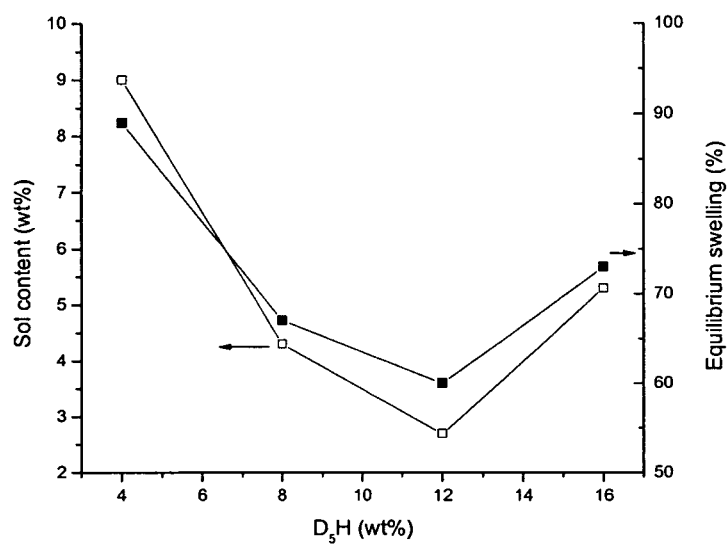
FIG. 19 is a graph of the sol contents and swelling ratios of APCNs prepared from a G50-1600 graft with different crosslinker concentrations (4, 8, 13, and 16%)

The Effect of Crosslinker ($D_5H$ or PMHS) Concentration:

Since, in some embodiments, the extent of crosslinking is critical for APCN properties, experiments are carried out to determine optimum crosslinker concentrations. The use of stoichiometric quantities of SiH relative to Si—CH=CH$_2$ gave insufficient crosslinking; however, charges with —SiH/Si—CH=CH$_2$ of approximately 5 (1 to 2 weight percent $D_5H$ or PMHP) gave co-networks with appropriate swelling and mechanical properties. A series of model experiments are carried out in which are added various amounts (from 4% to 15%) of $D_5H$ to V-PDMS-V charges and the extent of crosslinking is assessed by determining sol content and equilibrium water swelling (see Table 1). FIG. 19 summarizes these findings. The best overall results are obtained with approximately 12% $D_5H$. Similar experiments with PMHS (not shown) indicated optimum crosslinking with approximately 10% PMHS. These results are taken into consideration in the synthesis of APCNs.

Effect of the Molecular Weight of the [PDMAAm (PDMS)]-g-PDMS Graft Copolymer:

In one instance, the molecular weight of the graft can be controlled by the AIBN concentration, i.e., the $M_W$ of the product can be decreased by increasing AIBN concentration. Swelling data obtained with co-networks prepared from grafts made with different monomer/AIBN ratios (400, 800 and 1600) but crosslinked under identical conditions (grafts with 50% PDMAAm and crosslinked with 10% PMHS) indicate that co-networks prepared with higher molecular weight grafts exhibit lower water swelling ratios probably because of lower concentration of dangling PDMAAm chain ends (see Table 2).

Morphology Modification of APCNs by Blending and Extraction of Homo-PDMAAm:

High water uptake of immunoisolatory membranes is necessary for the rapid permeation of aqueous solutions. The present invention makes possible a procedure to increase the water permeability of APCN membranes by enlarging the volumes of the hydrophilic domains while maintaining domain bi-continuity. While not wishing to be bound to any one theory, it is believed that the hydrophilic domains in the present invention's APCNs could be enlarged and thus their permeabilities to aqueous penetrants increased by adding to graft charges homo-PDMAAm, crosslinking the charges, and after the morphology has stabilized, removing the added homo-PDMAAm from the APCN by extraction with water. The homo-PDMAAm is expected to blend with the network-PDMAAm and thus to increase the volume fraction of the hydrophilic domain. The enlarged hydrophilic volume fraction is permanently fixed upon crosslinking and renders the morphology more permeable to aqueous systems.

Thus a series of experiments is carried out in which 5.1, 9.6, 17.5 and 27.1 weight percent homo-PDMAAm is added to the charges, and after the morphology of the network has stabilized (i.e., after crosslinking) the added homo-PDMAAm is removed by water extraction. In this manner, one is able to more than double the swelling ratio of the membranes without increasing the amount of covalently linked PDMAAm (increasing the amount of network-PDMAAm would have reduced the volume fraction of PDMS, which is undesirable). Membranes modified by this technique exhibited much higher water swelling (see the data in Table 2), and glucose and insulin permeabilities.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A method for producing an implantable device for providing insulin comprising:
   (A) providing at least one implantable device for producing insulin, the device comprising:
      a perforated mid-section bound at the edges thereof by a seal wherein the perforated midsection includes a pattern of perforations;
      and at least one filling port designed to permit the perforated mid-section to be filled with insulin producing cells;
   (B) depositing on the perforated mid-section a biologically compatible polymer network; and
   (C) forming at least one immunoisolatory membrane on the perforated mid-section with a biologically compatible polymer network deposited thereon;
   wherein the biologically compatible network is a nanomat formed from electrospun polyurethane nanofibers.

2. The method of claim 1, wherein the insulin producing cells are porcine endocrine cells.

3. The method of claim 1, wherein the nanofibers have an average diameter of about 1 nanometer to about 25,000 nanometers.

4. The method of claim 1, wherein the at least one immunoisolatory membrane is formed from a crosslinked amphiphilic co-network.

5. The method of claim 4, wherein the crosslinked amphiphilic co-network is formed from a combination of poly(ethylene glycol), polydimethylsiloxane and tris(dimethylsilyloxy)-phenylsilane.

6. The method of claim 4, wherein the crosslinked amphiphilic co-network is formed from a combination of poly(N,N-dimethyl acrylamide), polydimethylsiloxane and polymethylhydrosiloxane.

7. The method of claim 1, wherein the at least one immunoisolatory membrane has bi-continuous hydrophilic and hydrophobic domains and hydrophilic pore dimensions in the range of about 3.0 nm to about 4.0 nm.

8. The method of claim 1, wherein the at least one immunoisolatory membrane is an amphiphilic water swollen membrane having bi-continuous hydrophilic pore dimensions in the range of about 3.0 nm to about 4.0 nm.

9. The method of claim 1, further comprising the steps of: (D) filling the device with a suitable amount of insulin producing cells; and (E) sealing the device.

10. The method of claim 1, wherein perforated mid-section is metal.

11. The method of claim 10, wherein the metal is selected from stainless steel, nitinol, tantalum, or titanium.

12. The method of claim 10, wherein a conductive metal wire or ribbon is inserted into the perforated mid-section.

13. The method of claim 12, wherein the metal is selected from stainless steel, nitinol, tantalum, or titanium.

14. The method of claim 1, wherein perforated mid-section is rotated during deposition of the biologically compatible polymer network.

15. The method of claim 1, wherein the perforated mid-section includes perforations having a diameter of 0.5 mm.

16. A method for producing an implantable device for providing insulin comprising:
   (a) providing at least one implantable device for producing insulin, the device comprising:
      a perforated mid-section bound at the edges thereof by a seal, wherein the perforated midsection includes a pattern of perforations; and
      at least one filling port designed to permit the perforated mid-section to be filled with insulin producing cells;
   (b) depositing on the perforated mid-section a biologically compatible polymer network;
   (c) forming at least one immunoisolatory membrane on the perforated mid-section with a biologically compatible polymer network deposited thereon;
   (d) implanting the device into a diabetic mammal;
   (e) filling the device with a suitable amount of insulin producing cells; and
   (f) sealing the device to yield the insulin producing device wherein the biologically compatible network is a nanomat formed from electrospun polyurethane nanofibers.

17. The method of claim 16, wherein the insulin producing cells are porcine endocrine cells.

18. The method of claim 16, wherein the nanofibers have an average diameter of about 1 nanometer to about 25,000 nanometers.

19. The method of claim 16, wherein the at least one immunoisolatory membrane is formed from a crosslinked amphiphilic co-network.

20. The method of claim 19, wherein the crosslinked amphiphilic co-network is formed from a combination of poly(ethylene glycol), polydimethylsiloxane and tris(dimethylsilyloxy)-phenylsilane.

21. The method of claim 19, wherein the crosslinked amphiphilic co-network is formed from a combination of poly(N,N-dimethyl acrylamide), polydimethylsiloxane and polymethylhydrosiloxane.

22. The method of claim 16, wherein the at least one immunoisolatory membrane has bi-continuous hydrophilic and hydrophobic domains and hydrophilic pore dimensions in the range of about 3.0 nm to about 4.0 nm.

23. The method of claim 16, wherein the at least one immunoisolatory membrane is an amphiphilic water swollen membrane having bi-continuous hydrophilic pore dimensions in the range of about 3.0 nm to about 4.0 nm.

24. The method of claim 16, wherein the device is implanted in subcutaneous loci.

25. The method of claim 16, wherein the device is implanted in intraperitoneal loci.

26. The method of claim 16, wherein the device is replenished with additional tissue cultures of insulin producing cells.

27. The method of claim 16, wherein perforated mid-section is metal.

28. The method of claim 27, wherein a conductive metal wire or ribbon is inserted into the perforated mid-section.

29. The method of claim 16, wherein perforated mid-section is rotated during deposition of the biologically compatible polymer network.

30. The method of claim 16, wherein the perforated mid-section includes perforations having a diameter of 0.5 mm.

* * * * *